United States Patent [19]

Sebastian et al.

[11] Patent Number: 5,437,697
[45] Date of Patent: Aug. 1, 1995

[54] METHOD TO IDENTIFY GENETIC MARKERS THAT ARE LINKED TO AGRONOMICALLY IMPORTANT GENES

[75] Inventors: Scott A. Sebastian, Hockessin, Del.; Scott V. Tingey, Elkton, Md.; Michael K. Hanafey, Wilmington, Del.

[73] Assignee: E. I. Du Pont de Nemours and Company, Wilmington, Del.

[21] Appl. No.: 97,349

[22] Filed: Jul. 23, 1993

Related U.S. Application Data

[63] Continuation-in-part of Ser. No. 909,833, Jul. 7, 1992, abandoned.

[51] Int. Cl.⁶ .......................... A01H 1/00; A01H 1/02; A01H 5/00; C12N 15/00
[52] U.S. Cl. .......................................... 47/58; 435/6; 435/172.1; 800/200
[58] Field of Search .................. 800/200, DIG. 26; 435/172.3, 172.1, 6; 935/92, 93, 94, 96, 98; 47/58

[56] References Cited

FOREIGN PATENT DOCUMENTS

WO89/07647 8/1989 WIPO .......................... C12N 15/00

OTHER PUBLICATIONS

Muehlbauer et al. 1991. Theor Appl Genet. 81:189–198.
Soller et al. 1983. Theor. Appl Genet. 67:25–33.
Beckman et al. 1986. Oxford Surveys of Plant Molecular & Cell Biology, vol. 3. pp. 196–250.
Grabau et al. 1992. Crop Science. 32:271–274.
Keim et al. 1990. Genetics. 126:735–742.
Grabau et al. 1989. Crop Sci. 29:1554–1559.
Shoemaker et al. 1992. Crop Sci. 32:1091–1098.
Patterson et al. 1991. Advances in Agronomy. vol. 46:40–90.
Ayala et al. 1980. Modern Genetics. pp. 783–791 and 795–796.
Delannay et al. 1983. Crop Science. 23:944–949.
Stuber, C. W. et al, *Crop Science*, 22, 737–740, (1982).
Stuber, C. W. et al, *Genetics, 95, 225–236, (1992).*
Tekrony et al, In Soybeans: *Improvement, Production and Uses*, 2nd edition, ASA No. 16, 295–297, (1987).
Menancio et al, *TAG*, 79, 235–240, (1990).
Tingey et al, *Journal of Cellular Biochemistry, Supplement* 14E, 291, Abstract No. R153, 1990.
Beckmann et al, *TAG*, 67, 35–43, (1983).

*Primary Examiner*—David T. Fox
*Assistant Examiner*—Erich E. Veitenheimer

[57] ABSTRACT

A novel method of identifying genetic markers linked to allels conferring yield potential of a crop species has been developed. By conducting genetic marker analysis of a set of current elite lines and the ancestral population from which they were derived by decades of plant breeding, one can determine and compare the expected and observed allele frequencies within elite populations at numerous polymorphic loci. Since the traditional plant breeding effort has consistently utilized yield as a selection criteria, deviations from expected allele frequency at certain loci have been used to identify alleles that confer yield potential. Agronomically superior progeny can, therefore, be selected utilizing genetic markers.

5 Claims, 1 Drawing Sheet

METHOD TO IDENTIFY GENETIC MARKERS THAT ARE LINKED TO AGRONOMICALLY IMPORTANT GENES

RELATED APPLICATION

This application is a continuation-in-part of application U.S. Ser. No. 07/909,833 filed Jul. 7, 1992, now abandoned.

BACKGROUND OF THE INVENTION

This invention is in the field of the plant breeding and molecular biology. More specifically, the invention concerns a method to identify and use genetic markers that are diagnostic of plant genes conferring agronomic fitness to crop plants.

All crop species are grown for the purpose of harvesting some product of commercial significance. Enhancement of productivity or "yield" of that product is almost invariably a major goal of any plant breeding program. Yield is the final culmination of many distinguishable agronomic traits such as emergence vigor, vegetative vigor, disease resistance, seed set, standability, and threshability. Hence, the terms "yield" and "agronomics" are often used interchangeably. Obviously, yield is a quantitative (non-discrete) trait that is influenced by many genetic and environmental factors. The greatest barrier to progress in selection for quantitative traits, especially for yield, is the lack of repeatability of phenotypic traits in different environments. Although genetic differences in yield potential undoubtedly exist among individuals, environmental effects make it difficult to identify genetically superior individuals. Hence, identifying individuals with the most favorable genotype is one of the most difficult and challenging aspects of plant breeding.

The breeder uses two main strategies to reduce the effect of environment on selection of genetically superior crop plants. By comparing individuals in enough different environments one can obtain an average measure on phenotype, or, by developing methods to bypass environmental effects, one can obtain a direct measure of genotype. Methods to directly assay genotype are obviously preferred and exemplify the true art and science of plant breeding.

Although there is much speculation, the exact biochemical nature of genes affecting yield is largely unknown. This has made it very difficult to identify the exact quantitative trait loci (QTL's) that affect yield. However, it is possible to identify and monitor segregation of discrete (qualitative) genetic markers that are closely linked to QTL's. A "genetic marker" is any qualitatively inherited phenotype that can be used to monitor the segregation of alleles that are genetically linked to the marker. Genetic markers can, therefore, be used as a direct measure of genotype at a linked locus (e.g., a QTL) that may otherwise be difficult to score. Genetic markers include visual traits such as flower color, enzyme variants such as isozymes, blood groups (in animals), and molecular markers such as restriction fragment length polymorphisms (RFLP's) or randomly amplified polymorphic DNA (RAPD's).

In order for a QTL to be identified or mapped to a specific chromosome location, the geneticist must first demonstrate that the quantitative trait of interest is highly correlated with a genetic marker. This correlation is the basis for the assumption of genetic linkage between the marker and the QTL. The conventional approach to mapping QTL's involves making a cross between two plants that are genetically different for one or more characters of interest, and obtaining segregating progeny (commonly F2, backcross, or recombinant inbred lines) from the hybrid. A number of progeny (usually >100) are evaluated for the character of interest and for their genotypes at marker loci at regular intervals (10-20 cM) throughout the genome. A search is then made for associations between the segregating markers and the character of interest. If such associations are found, they should be due to linkage of the marker to a gene(s) affecting the character.

Obviously, a key assumption of such conventional QTL analysis is that the quantitative trait phenotype in question can be measured with as little error and ambiguity as possible. However, individual measurements for traits such as yield are typically confounded with experimental error and environmental effects. Conventional mapping of QTL's for yield, therefore, requires costly and time consuming replicated yield testing of each segregating progeny over many environments so that each individual is assigned an average measure of phenotype that is reliable. Only then can meaningful correlations be made between yield genes and qualitative markers. Another major weakness of conventional QTL analysis is the fact that conclusions can only be made about genetic variation that exists within the segregating population that is being studied. This is extremely limiting for a trait such as yield since no subpopulation will contain the myriad of yield genes available to the plant breeder. These two weaknesses are exemplified by two previous attempts to find genetic markers for yield genes.

Grant et al. (International Patent Application Number WO 89/07647, 1989) applied conventional QTL analysis to identify molecular markers that were diagnostic of yield and other specific agronomic traits that contribute to yield in maize. Segregants from the cross B73×Mo17 were evaluated for quantitative traits based on evaluation of F3 topcrosses and bulk F4 progenies derived from F2 plants. To determine phenotype, each F3 topcross or F4 bulk progeny was grown in two replications at each of four environments. Because genotype by environment interactions were observed for all traits, correlations between probes and quantitative traits had to be determined for each location separately. This means that correlations could only be based on two data points per segregant, and while statistically significant correlations between traits and markers were reported, there is no evidence that selection based on these markers is effective. Based on their limited phenotypic data, especially for yield, it is highly questionable whether meaningful correlations have been established.

In an earlier attempt to find genetic markers for grain yield in maize, Stuber et al. (*Genetics* 95: 225-236 (1980) and *Crop Science* 22: 737-740 (1982)) measured the frequency of alleles at 20 isozyme loci in two open-pollinated populations before and after recurrent selection for yield. They showed that changes in allele frequency at 8 such loci were associated with changes in grain yield that resulted from traditional selection based on yield. Such converse selection based on "favorable" isozyme alleles resulted in only slight yield gains, however, when compared to selection based on yield per se. When results were averaged over environments, marker-assisted selection resulted in yield progress of only 2 to 3% while selection based on yield per se resulted in approximately a 30% yield increase. These experiments exemplify the problems associated with obtaining reliable yield data, the limitation of conclusions to the two varieties of maize being studied, and the difficulty of finding markers that are diagnostic of yield. Such results actually denigrate the assumption that significant yield progress can be accomplished through marker-assisted selection. The accuracy of Stuber et al.'s statistical methods are highly dependent on the practice of randomly mating selected individuals during each cycle of recurrent selection. In practice, it is difficult to enforce a mating system that is truely random. This is a serious limitation of conventional population genetic studies.

A key feature of the current invention is a population genetic study that employs genetic markers to measure allele frequency differences between modern-day elite lines and their earliest known ancestors. Since Applicants' statistical analyses are calibrated with known pedigrees, the invention can be used to study changes in allele frequency in populations developed through non-random matings (the predominant type of mating used to breed crop plants). The invention completely eliminates the need to collect exhaustively replicated yield data or other quantitative data from segregating populations. Instead of relying on data collected from specific populations in specific environments, the current invention takes advantage of yield progress that has occured during the entire period that a crop has been domesticated. Indirectly, the invention relies on an extremely large pool of yield data that has already been collected through the past efforts of many plant breeders. Such data represents the performance of many different genotypes (allele combinations) over many different environments. Alleles that confer high yield over many environments have been favored by selection during the historical domestication of any crop plant. The observed frequency of favorable alleles in a collection of modern elite lines must, therefore, be greater than the frequency expected from random segregation of alleles from ancestors. The current invention takes advantage of differences between observed and expected allele frequency to identify alleles that affect yield thereby enabling the selection of high yielding progeny without exhaustive field testing. The invention also provides the opportunity to locate and clone alleles affecting yield in a positive manner. These alleles can then be used to transform existing crop plants to create new elite lines.

SUMMARY OF THE INVENTION

A method to rapidly identify alleles conferring agronomic fitness to a crop plant has been discovered. The method comprises:

a) selecting a sample of current-day elite lines of a given crop to form an elite population;

b) selecting the predominant and earliest known ancestral lines of said elite lines by considering the pedigrees of said elite lines;

c) conducting a genetic marker survey to determine the genotype of said elite lines and said ancestral lines;

d) using the pedigrees of said elite lines and genotypes of said ancestral lines to calculate the probability of each elite line inheriting each allele from said ancestral lines;

e) calculating the expected allele frequency of each allele within said elite population by averaging the probabilities calculated in step d) for each elite line;

f) calculating the observed allele frequency within said elite population; and g) comparing said observed allele frequency with said expected allele frequency for each said allele in said elite population to identify alleles at each locus that have been inherited more frequently than expected;

such that new crop plants with superior agronomic fitness can be efficiently identified with said genetic markers that are diagnostic of said alleles that have been inherited more frequently than expected. Preferred, by virtue of the ease of identifying ancestral lines, are soybean and corn (maize). However, Applicants' methods are applicable to any crop species for which:

1) the pedigrees of elite lines are largely known so that the genetic contribution of ancestors can be calculated, and 2) viable seed or tissue of the predominant ancestors of elite lines is available for determination of genotype.

DETAILED DESCRIPTION OF THE INVENTION

Definitions

Figure 1:
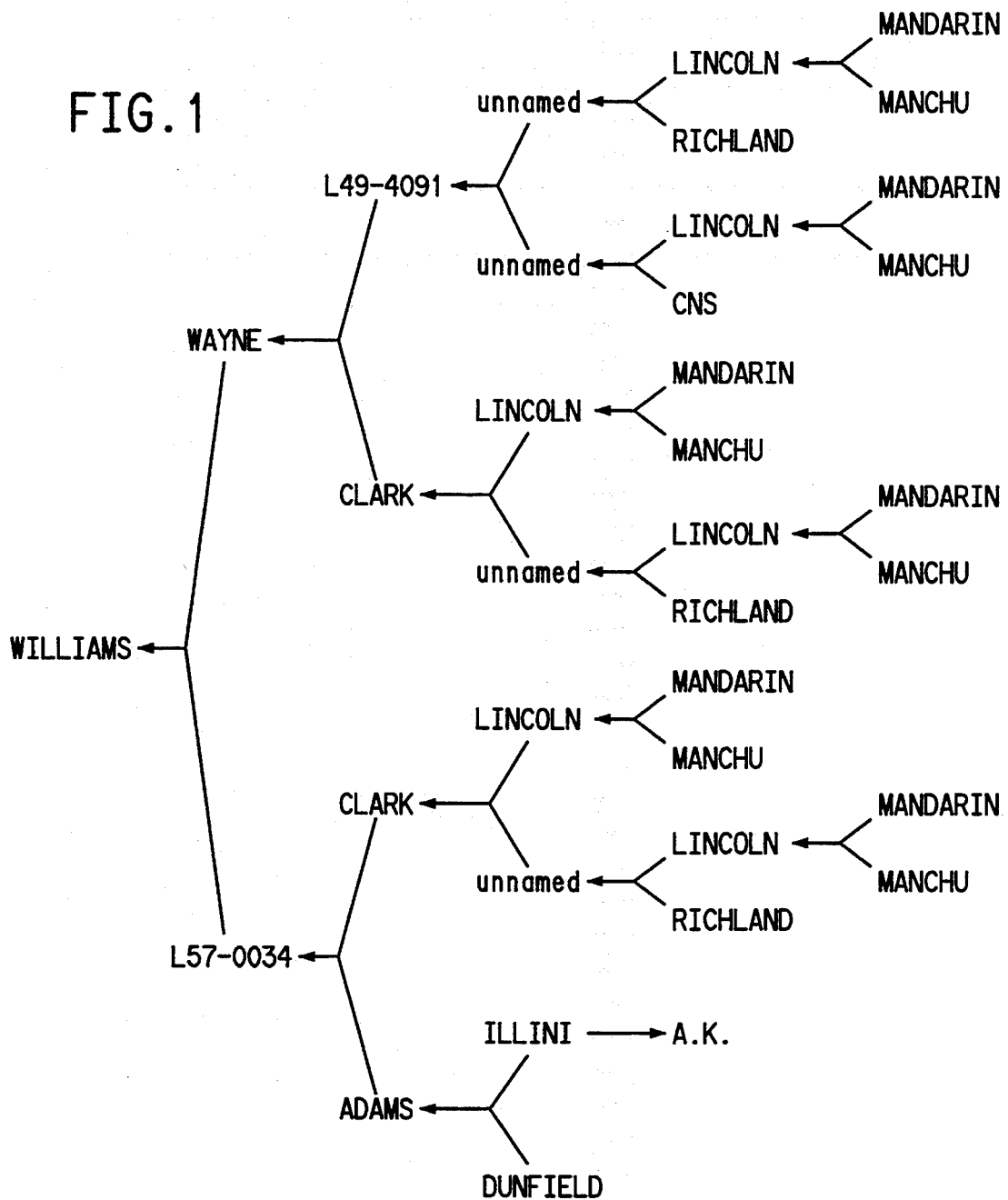
FIG. 1 is a diagramatic pedigree of an actual elite soybean line. This is used to illustrate how each ancestral line contributed to the parentage of Williams. Such diagrams can be used to calculate the coefficient of parentage of each ancestor in each elite soybean line.

In the context of this disclosure, the term "yield" refers to the productivity per unit area of a particular plant product of commercial significance. For example, yield of soybean is commonly measured in bushels of seed per acre or metric tons of seed per hectare per season. In a forage crop like alfalfa, yield refers to the weight of harvestable foliage per unit area. Yield is affected by both genetic and environmental factors. The main foci of this disclosure are the genetic factors within a given species that affect yield. "Agronomics", "agronomic traits", and "agronomic fitness" refer to the traits (and underlying genetic factors) of a given plant variety that contribute to yield over the course of growing season. Individual agronomic traits include emergence vigor, vegetative vigor, stress tolerance, disease resistance, herbicide resistance, branching, flowering, seed set, seed size, seed density, standability, and threshability. Yield is, therefore, the final culmination of all agronomic traits.

"Gene" is a general term for a heritable sequence of DNA. "Locus" refers to a specific chromosome location in the genome of a species where a specific type of gene can be found. "Allele" refers to one of several different DNA sequences that can be found at a specific locus. For example, at a specific locus where a gene for growth habit can be found, one allele is a specific DNA sequence that codes for determinate growth habit while another allele is a different DNA sequence that codes for indeterminate growth habit. A "favorable allele" is the allele at a particular locus that confers the most agronomically desirable phenotype of all the alleles at that locus. "Allele frequency" refers to the frequency (proportional or percentage format) at which a specific allele appears at a specific locus within an individual, within a line, or within a population of lines. For example, regarding the allele "A", diploid individuals of genotype "AA", "Aa", or "aa" have allele frequencies of 1.0, 0.5, or 0.0, respectively. One can calculate the allele frequency within a line by averaging the allele frequencies of a sample of individuals from said line. One can calculate the allele frequency within a population of lines by averaging the allele frequencies of lines that comprise the population. For a population with a finite number of individuals or lines, an allele frequency can be expressed as a count of individuals or lines containing said allele. A "genetic marker" is any qualitatively (discretely) inherited phenotype that can be used to monitor the segregation of alleles that are genetically linked to the marker. Genetic markers include visual traits such as flower color, enzyme variants such as isozymes, blood groups (in animals), and molecular markers such as restriction fragment length polymorphisms (RFLP's) or randomly amplified polymorphic DNA (RAPD's). To reduce verbage within this disclosure, a genetic marker allele designation is used to name the allele of agronomic significance that is genetically linked to the marker. In reality, the marker locus may or may not be part of the agronomically important allele.

A "genetic map" is a diagram that shows the genetic linkage relationships among loci on chromosomes (or linkage groups) within a given species. "Mapping" is the process of defining the linkage relationships of loci through the use of genetic markers, populations that are segregating for said markers, and standard genetic principles of recombination frequency. A "map location" is a specific locus on a genetic map where an allele can be found within a given species.

"Codominant markers" reveal the presence of each allele (two per diploid individual) at a locus. "Dominant markers" reveal the presence of only a single allele per locus. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers are equally valuable. As populations become more heterozygous and multiallelic, codominant markers become more informative of genotype than dominant markers.

A "genotype" is the genetic constitution of an individual or group of individuals. Genotype is defined by a list of alleles at known loci that the individual has inherited from its parents. "Homozygosity" is a genetic state of an individual where the individual has only one type of allele at a given locus (e.g., a diploid individual with two copies of the same allele at a locus). "Heterozygosity" is a genetic state of an individual where the individual has more than one allele at a given locus (e.g., and diploid individual with one copy each of two different alleles). "Homogeneity" is a genetic state of a group where individuals within the group have the same genotype at one or more specific loci. "Heterogeneity" is a genetic state of a group where individuals within the group differ in genotype at one or more specific loci. A "line" is a group of individuals of identical parentage that are generally inbred to some degree and are generally homozygous and homogeneous at most loci. "Transgressive segregation" is an inheritance pattern that results in the performance (e.g., agronomic performance) of an individual that is either superior to its better parent or inferior to its worst parent. Desirable transgressive segregation is the case where the progeny are better than either parent. Transgressive segregation can also be measured in terms of the number of favorable alleles that an individual inherits in relation to the number of favorable alleles that each of its parents contains. An "ideal segregant" is a segregant from a specific cross that contains only favorable alleles at each defined locus that is segregating in the cross. The ideal segregant therefore, has the best possible genotype at known loci that can result from a cross between parents that differ in genotype at said loci. "Ideal genotype" refers to an individual containing the favorable allele at all loci known to affect agronomic performance. The ideal genotype is, therefore, the ideal segregant from a cross between parents that complement in terms of favorable alleles at all defined loci affecting agronomic performance.

An "elite line" is a genetically superior line that has resulted from many cycles of breeding and selection for superior agronomic performance. An "elite population" is an assortment of different elite lines that can be used to represent the state of the art in terms of agronomically superior genotypes of a given crop species. An "ancestral line" is a parent used as a source of genes for the development of elite lines. An "ancestral population" is a group of ancestors that have contributed the bulk of the genetic variation that was used to develop elite lines. "Descendants" are the progeny of ancestors that may be separated from their ancestors by many generations of breeding. For example, elite lines are the descendants of their ancestors. The "pedigree structure" defines the relationship between a decendant and each ancestor that gave rise to that decendant. A pedigree structure can span one or more generations, describing relationships between the decendant and it's parents, grand parents, great grand parents etc.

A "survey" or "genetic survey" or "genetic marker survey" is the process of determining and recording the genotype of individuals or lines (e.g., ancestral and elite lines) at any number of defined loci with the use of genetic markers.

A "crop" is any plant species that is grown for the purpose of harvesting some product of commercial significance. A "self-pollinating crop" is a crop species that produces seed predominantly through fertilization of each plant's egg with its own pollen. A "cross-pollinating crop" is a crop species that produces seed predominantly through fertilization of each plant's egg with pollen from a different plant within the species.

Applicants' methods are applicable to crops for which:

1) the pedigrees of elite lines are largely known so that genetic contribution of ancestors can be calculated, and
2) viable seed or tissue of the ancestors of elite lines is available for determination of genotype. Examples of preferred self-pollinating crop species for which Applicants' methods would apply are barley, chickpea, cowpea, field beans, field peas, millet, oats, peanut, potato, rice, sesame, soybean, tobacco, tomato, and wheat. Examples of preferred cross-pollinating crop species for which Applicants' methods would apply are alfalfa, corn, pearl millet, rye, sugar beet, sugarcane, and sunflower.

"Random mating" is the mating of individuals within a population in a way that insures the equal probability of any two individuals mating regardless of genotype. "Non-random mating" is any deviation from random mating in which specific crosses between individuals are preferred over others.

Selection of Lines to Represent the "Elite Population"

In order to determine which loci have been affected by selection for agronomics, it is necessary to compare modern elite lines with their ancestors. Selection of elite lines for the survey should be done first since this will ultimately determine which ancestral lines should be surveyed. The number of elite lines chosen for the survey is dependent on how diverse the gene pool is for the crop in question. Since domesticated soybeans are known to have a fairly narrow gene pool and have been selected to fairly stringent standards, a rather small sampling of elite lines (12) was considered adequate for the soybean example disclosed herein.

If the elite lines are inbred sufficiently, each line will be quite homozygous and homogeneous at any given locus. However, depending on the generation at which an elite line was selected, there may be exceptions to this generalization. Although individual plants within a given line may be homozygous, they may not all be homozygous for the same allele at every locus. Such heterogeneity may be common within elite lines of certain crop species. However, within self-pollinating species, this heterogeneity will be rare and of little consequence to the genetic analysis. Either way, the investigator should be aware that not all "inbred" lines are compeletely homogeneous at every locus.

Selection of Lines to Represent the "Ancestral Population"

Once the elite lines have been chosen, one can then determine the relevant ancestral population from which said elites were derived. Although a comprehensive genetic marker survey of all known ancestors of an elite population may be desirable, a more practical survey can focus on ancestors that were used most frequently by breeders to develop the elite population. Hence, it is necessary to trace the pedigree of each elite line and determine the earliest known ancestors. Once the pedigree is obtained, the genetic contribution of each ancestor can be converted into a proportional or percentage format. Selection of the most important ancestors for the marker survey can then be based on average parental contribution to the elite population.

A proportional or percentage format assumes that an average of 50% of each parent's genome will be passed on to each progeny as a result of a two-way cross with another parent. For example, according to the diagramatic pedigree of the soybean line "Williams" (shown in FIG. 1), Williams should be 50% Wayne and 50% L57-0034. Wayne should be 50% L49-4091 and 50% Clark and so on. By tracing the pedigree back until no more branch points are found, the earliest known ancestors can be identified and their contribution to each elite line calculated. From FIG. 1, one can see that the earliest known ancestral lines of Williams are Mandarin, Manchu, Richland, CNS, A.K. and Dunfield. Assuming 50% genetic contribution from each parent in each two-way cross, one can calculate the percentage of genes in Williams that trace back to each of the earliest ancestral lines. According to pedigree, Williams is 25% Mandarin, 25% Manchu, 18.8% Richland, 6.3% CNS, 12.5% A.K., and 12.5% Dunfield. Such calculations can be computerized by anyone skilled in the art of plant breeding. The above ancestral analysis should be done for each of the elite lines included in the genetic survey. Percentages can be converted to proportions by dividing each percentage by 100.

Once the ancestral contribution to each of the sampled elite lines has been determined, one can select a pool of ancestral lines that represent the major genetic contribution to the elite gene pool. For example, it was found that 11 ancestral soybean lines accounted for 71% of the parentage of the 12 elite soybean lines chosen for the examples in the present application. Hence, these 11 ancestral lines contributed a major portion of the gene pool from which the elite population was derived.

Genetic Marker Survey of Elite and Ancestral Populations

Once the appropriate elite and ancestral lines have been chosen, the genotype of each line can be determined through the use of genetic markers. Genetic markers include any qualitative phenotype that can be used as a direct measure of genotype at a specific locus. Such markers include visual traits such as flower color, enzyme variants such as isozymes, and molecular markers such as restriction fragment length polymorphisms (RFLP's) or randomly amplified polymorphic DNA (RAPD's). Applicants have employed the use of RFLP's and RAPD's to determine genotype in the following examples. Experimental details for the RFLP and RAPD analyses are included in the examples.

Regardless of which genetic markers are used to monitor genotype, the end result is a marker genotype for each of the elite and ancestral lines. The genotype of each line is merely an indication of which allele the line possesses at any number of loci defined by said genetic markers. Loci that are monomorphic (i.e., only one allele is detectable) among any of the elite or ancestral lines are useless for Applicants' invention. Attention should be focused on loci for which polymorphism can be detected.

The specific markers used by Applicants in the current disclosure are merely a random subset of a nearly limitless set of potential genetic markers that could have been used to illustrate Applicants' invention. A collection of genetic markers for soybean is publicly available from Linkage Genetics (151 West 2200 South, Suite C, Salt Lake City, Utah 84119, 801-975-1188). A random set of genetic markers from such a publicly available source can be used by anyone skilled in the art to practice Applicants' invention.

Applicants have deposited the following twenty (20) probes in the American Type Culture Collection (ATCC), Rockville, Md. 20852-1776 on Mar. 8, 1995 under the terms of the Budapest Treaty. The probes with their ATCC accession numbers are as follows: 1148 (ATCC 97080), 1159 (ATCC 97081), 1202 (ATCC 97082), 1203 (ATCC 97083), 1318 (ATCC 97084), 1329 (ATCC 97085), 1342 (ATCC 97086), 1409 (ATCC 97087), 1443 (ATCC 97088), 1450 (ATCC 97089), 1487 (ATCC 97090), 1492 (ATCC 97091), 1503 (ATCC 97092), 1522 (ATCC 97093), 1525 (ATCC 97094), 1529 (ATCC 97095), 1587 (ATCC 97096), 1593 (ATCC 97097), 1596 (ATCC 97098), and 1610 (ATCC 97099).

Once the marker data is collected for the population of ancestral and elite lines, the next step is to determine how many genetic loci are represented by the polymorphism observed. In the case of RFLP and RAPD markers, gel bands are used to define genetic loci based on the probe that was used and on the banding pattern that exists among lines that are presumed to be predominantly homozygous and homogeneous at any given locus. The fact that each inbred line (in most cases) is homozygous for only one allele at a given locus can be used as a quick test of allelism. For example, if RFLP probe A identifies two different gel bands, and the two bands are mutually exclusive (i.e., each inbred line has only one of the two possible bands), the two bands can be assumed to identify alleles at a given locus. Allelism can be confirmed by segregation analysis. This is done by crossing two lines that are homozygous but contain different alleles at the locus in question. One can then monitor segregation of the alleles in segregating generations to test for expected Mendelian segregation patterns. Such confirmation is not essential for the purposes of the present application. Homology of DNA fragments to the same probe and mutual exclusivity among diverse inbred lines is a reasonable test of allelism for the purposes of Applicants' invention.

One of the main differences between RFLP and RAPD markers is the fact that RFLP's are largely codominant markers and RAPD's are usually dominant markers (Williams et al., Nucleic Acid Research 18: 6531-6535 (1990)). This does not affect the utility of either marker for this type of survey. However, it does affect the nature of the data. If polymorphism is observed at a given locus, an RFLP probe will usually identify at least two different bands of DNA that correspond to two different alleles at said locus. RAPD's, however, will usually identify polymorphism as the presence or absence of a "dominant" band which corresponds to the presence or absence of only one of the possible alleles at a given locus. Although there is no easy way to tell if another allele is present when the dominant band appears, the homozygous condition can generally be assumed when working with inbred lines. With most RAPD's, the absence of a band indicates that "another allele" is present. Depending on the desirability of the allele linked to the dominant band, selection is practiced either "for" or "against" the allele. It should be recognized that "dominance" in terms of genetic markers has nothing to do with the conventional meaning of dominance in terms of gene action. The gene action of an allele that is linked to a "dominant" marker is completely independent of the marker itself.

Many times, a single molecular probe will identify two or more different loci that share some sequence homology. This does not affect the test for allelism if the two loci segregate independently; mutual exclusivity of alleles within each locus still applies if homozygous and homogeneous lines are assayed.

Occasionally, a supposedly "inbred" line may show both allelic bands. For this reason, the geneticist should be aware of the possibility that an "inbred" line may actually be a mixture of related homozygous individuals that are heterogenous (homozygous for different alleles) at a few loci. This can result when a line is derived from a partially inbred individual (e.g. F4 or F5 generation) that appears homogeneous but may actually be segregating at some loci. Since DNA samples of a given line are usually derived from several individuals within that line, both alleles may be observed if the line is segregating at a specific locus. This explanation should be considered when an exception occurs in an otherwise obvious trend of mutual exclusivity of bands within elite lines.

The end result of the above survey is a list of ancestral and elite genotypes at loci defined by genetic markers. The genotypes of ancestral lines are needed to calculate the probability of inheriting each allele within the elite population ("expected allele frequency"). The genotypes of elite lines are needed to calculate the actual allele frequency within the elite population ("observed allele frequency").

Pedigree Analysis to Calculate Probability of Inheriting Each Allele in Each Elite Line Once one has determined the genotypes of ancestral and elite lines, statistical analyses are required to determine whether selection for agronomics has favored alleles at certain loci. The first statistic to calculate is the probability of finding each allele within the elite population with the assumption that selection had no effect on allele frequency. This expected allele frequency within the elite population serves as a basis for comparison to the observed allele frequency.

Expected allele frequency within the elite population is a function of the genotype of each ancestor and the pedigrees of elites lines representing the elite population. In a random mating population, the allele frequency among descendants should be similar to allele frequency among ancestors unless breeding and selection has favored certain alleles. However, since breeding of many crops (including soybeans) is not done through random mating, one must use the pedigree of each descendant (e.g., elite line) to calculate the probability of inheriting a given allele from its ancestors. Since it is impossible to determine whether selection has favored a given allele based on the genoytpe of only one descendant, one must study enough descendants to obtain a reliable measure of allele frequency. Within non-random mating populations, expected allele frequency can be obtained by averaging the individual probabilities of inheriting an allele over any number of descendants (that may differ greatly in pedigree).

Figure 2:
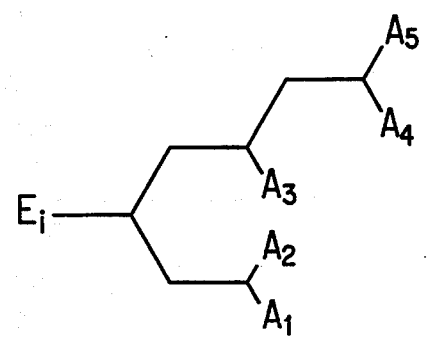
FIG. 2 is a generalized pedigree example used to illustrate the relationship between an elite line ($E_i$) and its ancestors ($A_i$).

Given several elite pedigrees (generalized in FIG. 2), it is assumed that the $A_i$ are mostly homozygous, and that at each cross in the pedigree, the $F_l$ is selfed several times so that each node in the pedigree is also mostly homozygous, including the final product, $E_i$.

At several loci (assumed independent, i.e. not linked), genotype is characterized by a marker:

$$M_{l,j} = \begin{matrix} 1 \\ 0 \end{matrix} \qquad 1$$

The "1" indicates presence of the allele, i.e., a specific marker phenotype, and "0" indicates absence of the allele, i.e., another marker phenotype. The subscript l indicates locus, and the subscript j indicates an individual line. In cases where a line is segregating at a locus, $M_{l,j}$ can be an intermediate value between 0 and 1.

From the pedigrees, the coefficient of parentage $C_{j,i}$ of each ancestor, j, in each elite, i, can be calculated. The probability of finding a "1" at a locus in an elite, under the null hypothesis of no selection during development of the elite is:

$$P_{1,i} = \sum_j^{Ancestors} C_{j,i} M_{1,j} \qquad 2$$

In many cases the accessible ancestors will not be complete, and this is reflected in:

$$\sum_j C_{j,i} < 1 \qquad 3$$

This is corrected for in an unbiased way by creating a hypothetical parent for each elite with coefficient of parentage:

$$r_i = 1 - \sum_j C_{j,i} \qquad 4$$

This is partitioned into two parts, a part that has the band, and a part that does not have the band, in a proportion determined by the fraction of known ancestors that have the band, $f_l$. The summation in equation 2 is adjusted for missing parentage by adding $r_i f_l$.

In a relatively small number of cases, the presence or absence of the band in an ancestor at a locus is unknown (missing data). In this event, $M_{l,j}$ is substituted with $f_l$.

Calculate the Expected Allele Frequency Among Elites

The probabilities of equation 2 are used to calculate the expected allele frequency ($A_l$) at a locus within the elite population under the null hypothesis that no allele was favored by selection:

$$A_1 = \frac{\sum_i^{Elites} P_{1,i}}{n} \qquad 5$$

where n = the number of elite lines with data at said locus. $A_l$ can be converted into the expected count ($x_l$) of elite lines with a given allele by multiplying $A_l$ by n.

$$x_l = nA_l \qquad 6$$

Calculate the Observed Allele Frequency Within Elite Population

The observed allele frequency ($O_l$) for a given allele within the elite population can be expressed as a count which is the sum of individual elite allele frequencies:

$$O_1 = \sum_j^{Elites} M_{1,j} \qquad 7$$

Comparison of the Observed Allele Frequency Among Elites to the Expected Allele Frequency The observed count for each allele among elites ($O_l$) is then compared to the expected count for that allele. A chi-square test is used to determine the significance of deviations from expected allele count within each locus:

$$c_1^2 = \Sigma \frac{(O_1 - x_1)^2}{x_1} \text{ (Sum over alleles at a locus)} \qquad 8$$

For cases where the probability of inheriting an allele in each pedigree is the same, the distribution of the number of occurances of the allele, r, is binomial. If the sample size is large enough this distribution becomes normal, and then a simple chi-squared test for significance can be made where degrees of freedom = number of alleles at the locus − 1. The hypothesis of no selection can be rejected for loci where the upper tail cumulative probability at chi-square is small enough.

A More General Approach to the Comparison of the Observed Allele Frequency Among Elites to the Expected Allele Frequency by the Generalized Binomial Distribution In those cases where the probability of inheriting an allele within each elite pedigree is not the same due to differences in the pedigree structure of each elite line, a more appropriate approximation of the probability of inheriting an allele can be obtained as follows. As before, $P_{l,i}$ is the probability of inheriting a specific allele at locus l, for elite i, and the probability of seeing r alleles inherited at locus l, in N trials is calculated as follows:

There are $N!/((N-r)! \cdot r!)$ combinations of elites that have inherited a specific allele r times in N pedigrees. Let $a_{i,k} = 1$ only if elite i contributes a specific allele in combination k. The probability of the kth combination is then:

$$\prod_{i=1}^{N} \begin{pmatrix} P_{1,i} & (a_{i,k} = 1) \\ 1 - P_{1,i}, (a_{i,k} \neq 1) \end{pmatrix} \qquad 9$$

and the total probability is the sum of the probabilities of all combinations:

$$P(r,N,\vec{p}) = \qquad 10$$

$$\begin{bmatrix} \vec{a} = C(k,r,N) \\ k = 1, 2, \ldots \frac{N!}{(N-r)!r!} \end{bmatrix} \prod_{i=1}^{N} \begin{pmatrix} P_{1,i} & (a_{i,k} = 1) \\ 1 - P_{1,i}, (a_{i,k} \neq 1) \end{pmatrix}$$

The function C(k,r,N) returns a vector of length N consisting of r "one" elements with the remainder "zero" elements, for the kth combination, and the outer sum indicates an iteration over all possible combinations.

If R specific alleles are observed in N elite pedigrees, and if R is larger than expected, the probability of observing R or more specific alleles inherited in N pedigrees is:

$$\sum_{r=R}^{N} P(r,N,\vec{p}) \qquad 11$$

The analogous equation when R is smaller than expected is:

$$\sum_{r=O}^{R} P(r,N,\vec{p}) \qquad 12$$

If one of these cumulative probabilities is small enough then the hypothesis that the results happened at random can be rejected, showing evidence for selection at locus l for a specific allele in N different pedigrees.

Computation of the General Case

This more general case is easily converted into a computer program, and the direct translation works for small problems (N<20) but fails for problems that at first glance might not appear to be significantly larger (e.g. N=50). The computational difficulty comes from the rapidly increasing number of combinations of r as N increases (the worst case is when r=N/2). For example, assume that the product part of Equation 10 can be computed in one microsecond, and that the summation takes negligible time. The computation of a N=20, r=10 case would take 0.185 seconds, N=30, r=15 would take 2.59 minutes, and N=50, r=25 would take 4 years.

One way around this combinatorial problem is to partition the set of probabilitits into groups. In the case of relatively shallow pedigrees with few total ancestors, it is likely that the probabilities for a set of N elites will partition without approximation into $N_p$ groups, where $N_p < N$. In this case the partitioned problem provides an equivalent but more efficient solution for the general case. If sufficient exact partitioning is not inherent in the set of probabilities, approximate partitioning can be done in which nearly equal probabilities are grouped and represented by the average of the members of the group. In this case the partitioned problem provides an approximation to the true solution.

Within each group, probabilities can be computed from the binomial distribution. If a group has $n_g$ members, then the probability of the group inheriting a specific allele $r_g$ times is binomial because each member has the same probability $p_g$, of inheriting the allele. The combinatorial problem is then, given the inheritance of a specific allele r times, how many different ways can these r cases be distributed over the $N_p$ groups, where each group could have inherited a specific allele at most $n_g$ times. An equation for the total number of such arrangements was not derived but a computer program that systematically enumerates the possible arrangements (without duplication) was written. As an example, consider a group of $N=24$ pedigrees, with the probabilities of inheriting an allele at a locus evenly spaced between 0.1 and 0.9 (24 different values). The results for three levels of partitioning are shown in Table 1.

TABLE 1

Probability calculation without approximation (columns labeled 24 groups), and with approximation by non-exact partitioning into groups of two (columns labeled 12 groups), and groups of four (columns labeled 6 groups). A dramatic reduction in computation time results (2nd row), without adding significant error

| | 24 groups 82 seconds | | 12 groups 2.4 seconds | | 6 groups 0.1 seconds | |
|---|---|---|---|---|---|---|
| r | log(p) | log(Σp) | log(p) | log(Σp) | log(p) | log(ΣP) |
| 0 | −8.83 | −8.83 | −8.81 | −8.81 | −8.74 | −8.74 |
| 1 | −7.18 | −7.17 | −7.16 | −7.15 | −7.11 | −7.10 |
| 2 | −5.87 | −5.85 | −5.86 | −5.84 | −5.82 | −5.80 |
| 3 | −4.78 | −4.75 | −4.78 | −4.74 | −4.75 | −4.71 |
| 4 | −3.87 | −3.81 | −3.86 | −3.81 | −3.84 | −3.79 |
| 5 | −3.09 | −3.02 | −3.09 | −3.01 | −3.07 | −3.00 |
| 6 | −2.44 | −2.34 | −2.44 | −2.34 | −2.43 | −2.33 |
| 7 | −1.91 | −1.77 | −1.91 | −1.77 | −1.90 | −1.76 |

Determine which Alleles were Favored by Selection for Agronomics

By comparing the observed frequency of a given allele in the elite population to the average probability of inheriting that allele (i.e., comparing observed count to expected count), one can determine which loci have been affected by historical selection for agronomic traits. Favorable alleles are identified simply as the ones that have been inherited more frequently than expected (i.e., have been favored by selection). Unfavorable alleles are those inherited less frequently than expected (i.e., selected against). A statistical test, as described above, can be used to establish the significance of a difference between observed and expected allele frequency.

Loci with significant deviations from expected allele frequency should be suspected of containing genetic variation for any trait for which there was consistent directional selection over the entire period of domestication. This is usually the case for loci affecting yield in most crops. In fact, high yield has been the only selection criterion used consistently by all breeding programs involved in the domestication of a particular crop. Since breeding programs vary greatly in testing environment, Applicants' method is particularly sensitive to alleles that confer general productivity over many environments. Such alleles are certainly among the most desirable in the development of new cultivars.

Use Important Markers to Select Agronomically Superior Plants

Once markers for agronomically important genes have been identified, these genes can be monitored and manipulated in the same ways as other genes that are qualitatively inherited. Examples of such applications include:

1) selection of parents that will produce superior transgressive segregants;
2) selection of superior lines from crosses that are segregating at QTL loci;
3) selection of parents that will produce the best hybrids;
4) purification of heterogeneous lines to fix favorable alleles; and
5) selection for and maintenance of heterogeneity that is desirable.

EXAMPLE 1

Identification of Molecular Markers Associated with Genes Conferring Agronomic Fitness in Soybean Selection of Soybean Lines that Represent the "Elite Population"

Asgrow Seed Company is recognized throughout the soybean seed industry as a leader in the development of high-yielding soybean lines. For this reason, a sampling of Asgrow's product line (circa 1989) was used to represent the "state-of-the-art" in terms of modern-day elite soybean germplasm. Representative Asgrow lines were chosen from each maturity zone to represent an elite population of soybeans. In addition, some key public soybean lines (Williams and Essex) were chosen because of their extensive use as parents in Asgrow's and many other soybean breeding programs. Although Williams and Essex are no longer the highest-yielding soybeans on the market, they have a proven record of adaptability to many environments within their respective maturity ranges. Several elite varieties (notably A3127 and A3966) that are significantly higher yielding than either parent have been developed from the cross Williams × Essex. Consequently, Williams and Essex are known to have good specific combining ability with each other. The elite lines included in the elite survey are shown in Table 2.

TABLE 2

ELITE AND ANCESTRAL SOYBEAN LINES USED IN MOLECULAR MARKER SURVEY

| LINE | POPULATION | RELATIVE MATURITY |
|---|---|---|
| A1937 | ELITE | 1 |
| A3127 | ELITE | 3 |
| A3205 | ELITE | 3 |
| A3307 | ELITE | 3 |
| WILLIAMS 82 | ELITE | 3 |
| A3966 | ELITE | 3 |
| A4271 | ELITE | 4 |
| A4595 | ELITE | 4 |
| A4906 | ELITE | 4 |
| A4997 | ELITE | 4 |
| A5474 | ELITE | 5 |
| ESSEX | ELITE | 5 |
| MANDARIN | ANCESTOR | 1 |
| MUKDEN | ANCESTOR | 2 |
| RICHLAND | ANCESTOR | 2 |
| MANCHU | ANCESTOR | 3 |
| A.K. | ANCESTOR | 3 |
| S100 | ANCESTOR | 5 |
| PI54610 | ANCESTOR | 6 |
| CNS | ANCESTOR | 7 |
| ROANOKE | ANCESTOR | 7 |
| TOKYO | ANCESTOR | 7 |
| STRAIN 171 | ANCESTOR | ? |

Selection of Soybean Lines that Represent the "Ancestral Population"

After selection of elite lines for the genetic survey, the pedigree of each elite line was traced back to the original ancestors. Based on the assumption that an average of 50% of a parent's genes are transferred to each progeny in any two-way cross, the proportion of each elite line's parentage tracing to each of the predominant ancestors (coefficient of parentage) is shown in Table 3. The proportion of each ancestor is averaged over all 12 elite lines and the mean is listed at the bottom of Table 3. The table is sorted from left to right by the ancestor used most (CNS) to the ancestor used least (Mukden). These 11 ancestors accounted for a total of 71% (total coefficient of parentage=0.71) of the pedigrees of the 12 elite lines (Table 3). This was considered to be a significant proportion of the ancestral gene pool for the purpose of the genetic marker survey.

Based on their contribution to the elite gene pool, the 11 ancestors (Tables 2 and 3) were selected to represent the "ancestral population". The existence of unrecognized, partial errors in the pedigree of an elite line (For example, the published pedigree of Lincoln utilized by Applicants is Mandarin×Manchu, see Bernard et al., USDA/ARS Tech. Bulletin No. 1746, Dept. Agronomy, U. Ill., 1988. Through personal communications, Applicants have discovered that some plant breeders express doubt as to the actual pedigree of Lincoln.) would have only a minor effect on the results of the statistical analyses used in establishing allele frequencies and no impact on the validity and utility of Applicants' invention.

TABLE 3

PROPORTION OF ELITE PARENTAGE CONTRIBUTED BY MAJOR ANCESTORS

| | CNS | MANDARIN | MANCHU | S100 | RICHLAND | ROANOKE | AKHAR | STRA171 | TOKYO | PI54610 | MUKDEN | TOTAL |
|---|---|---|---|---|---|---|---|---|---|---|---|---|
| | | | | | | coefficient of parentage for each ancestor | | | | | | |
| A1937 | 0.06 | 0.22 | 0.22 | 0.00 | 0.13 | 0.00 | 0.09 | 0.06 | 0.00 | 0.00 | 0.00005 | 0.78 |
| A3127 | 0.19 | 0.13 | 0.13 | 0.13 | 0.08 | 0.06 | 0.00 | 0.00 | 0.02 | 0.02 | 0.00 | 0.65 |
| A3205 | 0.13 | 0.15 | 0.15 | 0.06 | 0.15 | 0.03 | 0.03 | 0.00 | 0.007 | 0.007 | 0.06 | 0.78 |
| A3307 | 0.12 | 0.17 | 0.17 | 0.06 | 0.10 | 0.03 | 0.00 | 0.00 | 0.007 | 0.007 | 0.00 | 0.65 |
| A3966 | 0.19 | 0.13 | 0.13 | 0.13 | 0.08 | 0.06 | 0.00 | 0.00 | 0.02 | 0.02 | 0.00 | 0.75 |
| A4271 | 0.13 | 0.20 | 0.20 | 0.06 | 0.12 | 0.03 | 0.00 | 0.00 | 0.007 | 0.007 | 0.000001 | 0.75 |
| A4595 | 0.11 | 0.16 | 0.16 | 0.06 | 0.11 | 0.03 | 0.02 | 0.00 | 0.04 | 0.04 | 0.03 | 0.76 |
| A4906 | 0.17 | 0.07 | 0.07 | 0.13 | 0.04 | 0.06 | 0.10 | 0.05 | 0.02 | 0.02 | 0.0004 | 0.71 |
| A4997 | 0.16 | 0.00 | 0.00 | 0.13 | 0.0002 | 0.06 | 0.20 | 0.09 | 0.02 | 0.02 | 0.0002 | 0.67 |
| A5474 | 0.22 | 0.00 | 0.00 | 0.22 | 0.00 | 0.00 | 0.00 | 0.00 | 0.04 | 0.04 | 0.00 | 0.52 |
| WM82 | 0.06 | 0.26 | 0.26 | 0.00 | 0.16 | 0.00 | 0.00 | 0.00 | 0.00 | 0.00 | 0.00 | 0.74 |
| ESSEX | 0.31 | 0.00 | 0.00 | 0.25 | 0.00 | 0.13 | 0.00 | 0.00 | 0.03 | 0.03 | 0.00 | 0.75 |
| MEAN | 0.15 | 0.12 | 0.12 | 0.10 | 0.08 | 0.04 | 0.04 | 0.02 | 0.02 | 0.02 | 0.008 | 0.71 |

Genetic Marker Survey of Ancestral and Elite Soybean Populations

Once the elite and ancestral lines were selected for the survey, the genotype of each line was determined with the use of both RFLP's (from random genomic Pst I clones) and RAPD's that revealed DNA sequence based polymorphism in the soybean genome. The genetic map location of most of the RFLPs have been determined. In all cases below, soybean leaf tissue was collected from greenhouse-grown plants as the source of DNA.

DNA Isolation

Total genomic soybean DNA was prepared from 3 grams (dry weight) of lyophilized soybean leaves by a modification of the method of Murray and Thompson (Nucleic Acids Research 8: 4321–4325 (1980)), where only one CsCl gradient centrifugation was performed. Smaller scale soybean DNA preparation followed the procedure of Dellaporta et al. (Molecular Biology of Plants, pp. 36–37 1st ed., Cold Spring Harbor Laboratory, 1985), using 1 gram of fresh leaf tissue.

Preparation of Random Genomic Clones

DNA was digested with Pst I and separated on a preparative agarose gel. Gel sections containing fragments between 500 and 4000 bp were excised and the DNA extracted. The resulting Pst I fragments were ligated into the Pst I digested pBS+ vector (Stratagene), and the ligation products transformed into E. coli JM101. Plasmid DNA was prepared from ~4000 individual lac-transformants using a standard miniprep procedure (Maniatis et al., Molecular Cloning: A Laboratory Manual, Cold Spring Harbor Laboratory, 1982), digested with Pst I, and separated on a 0.8% agarose gel. A Southern blot was prepared (Maniatis et al., Molecular Cloning: A Laboratory Manual, Cold Spring Harbor Laboratory, 1982) and hybridized to 32P-labelled total soybean genomic DNA to identify clones that contain high copy number genomic DNA sequences. These were discarded and the remaining low copy number genomic clones were used as hybridization probes to detect polymorphism between Glycine max cultivar Bonus, and Glycine soja PI81762. Over 600 polymorphic random genomic clones were mapped in the soybean genome, following general methods outlined by Botstein et al. (Amer. J. Human Genet. 32: 314–331 (1980)), using an F2 population derived from a cross between Glycine max cultivar Bonus, and Glycine soja PI81762. As genetic map positions were determined for each hybridization probe, these probes were placed on Southern blots containing the above germplasm. In doing so, a genotype for each soybean line at several defined loci in the genome was obtained.

Genomic Blots

Restriction enzyme digestions were performed on five micrograms of soybean genomic DNA, in conditions recommended by the enzyme supplier, using 5–10 units of enzyme per 5 g of plant DNA. Restriction enzymes were chosen as appropriate for each polymorphism to be assayed. Agarose gel electrophoresis and Southern blotting were performed in standard conditions (Maniatis et al., Molecular Cloning: A Laboratory Manual, Cold Spring Harbor Laboratory, 1982). GeneScreen((Du Pont) or Hybond-N((Amersham) uncharged Nylon membranes were used for solid supports. After capillary transfer the DNA was UV-crosslinked to the membrane and baked at 80° C. as recommended by the manufacturer.

Preparation of Radioactive Probes 32P-labeled DNA probes were prepared from plasmid DNA, linearized by digestion with Pst I, by the method of Feinberg and Vogelstein (Anal. Biochem. 132: 6–13 (1983)). When large number of probes were handled simultaneously the probes were prepared in 96 well V-shaped microtiter plates using Beckman Instruments Biomek laboratory robot.

Hybridization and Autoradiography

Fresh blots were pre-hybridized in 1M NaCl, 50 mM Tris-HCl pH 7.5, 1% SDS, 5% dextran sulphate for several hours at 65° C. in stackable plastic drawer organizer boxes. 32P-labeled DNA probes were denatured through the addition of 125 microliters of a solution containing 75% formamide, 2.5 mg/ml of sheared, boiled, salmon testes carrier DNA, and incubation at 65° C. for 15 min. The probe was then added to the pre-hybridized blot and the hybridization was allowed to proceed at 65° C. for 20–24 hrs with gentle mixing in an air incubator. The blots were washed for 30 min each, at 65° C., in the following solutions: 2×SSPE, 0.1% SDS; 2×SSPE, 0.1% SDS; 2×SSPE, 1.0% SDS; 2×SSPE, 1.0% SDS; 0.5×SSPE, 0.1% SDS (20×SSPE is 3.6M NaCl, 200 mM NaH$_2$PO$_4$ pH 7.4, 20 mM EDTA (pH7.4) [Maniatis et al., Molecular Cloning: A Laboratory Manual, Cold Spring Harbor Laboratory, 1982]). Up to 20 blots, interleaved with a plastic window screen material, were washed simultaneously in a plastic box. Blots were placed in polypropylene project folders (C-Line Products) and autoradiographed using Kodak X-Omat AR film, for 18–100 hrs. Blots were reused up to ten times after stripping in 0.4N NaOH (30 min. at 42° C.) and washing in 0.2M Tris-HCl pH 7.5, 0.1×SSPE, 0.1% SDS (30 min. 42° C.).

RAPD Marker Scoring

RAPD markers were scored on isolated DNA using the procedures of Williams et al. [Nucleic Acid Research 18: 6531–6535 (1990)]. The sequence of the RAPD primers for each marker are as follows (nucleotide sequence is listed 5' to 3'): AP5C=CTGAAGTAC, AP5G=CTCATGCATC, AP8H=TGGTCACAGA, AP6=GCAAGTAGCT, AP8F=TGGTCTCTGA, AP4C=TCTCGATGCA, AP5B=CTCTTGCTAC, AP3C=TCCTAGCCAA, AP5=CTGATGCTAC, AP5H=CACATGCTTC, AP7=CTGATACGGA, AP8B=TCGTCACTGA.

Tables 4A and 4B show the polymorphism that was found among the 11 ancestral and 12 elite soybean lines, respectively. Loci and alleles defined by RAPD's begin with the designation "AP". Loci and alleles defined by RFLP's begin with an arabic numeral designation. The restriction enzymes used to reveal the polymorphism are designated as "E1" (Eco RI), "E5" (Eco RV), and "H3" (Hin dIII). Within most lines, the band (allele) was either present (allele frequency=1) or absent (allele frequency=0). Missing data indicates that the score was not readable. When used to probe DNA from the soybean lines, most RFLP probes for which polymorphism was observed identified 2 polymorphic bands of DNA. Two out of 20 probes (1202 and 1596) identified 3 polymorphic bands and one RFLP probe (1318) identified 4 polymorphic bands. With few exceptions, when two or three polymorphic bands were observed per probe, only one of the bands was present in any given soybean line. This is typical of what to expect if the probe identifies two or three different alleles at one locus and the soybean lines are inbred enough to be homozygous and homogeneous. One RFLP probe (1318) identified 4 different bands. Based on their patterns of mutual exclusivety, two of the 4 bands represented alleles at one locus and the other 2 bands represented alleles at a second locus. Hence probe 1318 was diagnostic of 2 different polymorphic loci. Based on such observations, each RFLP band was assigned an allele designation at a specific locus (Tables 4A and 4B). Any probe that failed to detect polymorphism among either elite or ancestral lines was excluded from the dataset due to the lack of useful information provided by such probes. The few exceptions where an elite line contained more than one allele per locus was assumed to be due to heterogeneity at that locus within the line. Given that many elite lines are derived from F3 to F5 selections of a cross, it is reasonable to assume that at least some genetic heterogeneity exists within lines. In such cases, the frequency of each allele within the line was assumed to be 0.5 instead of either 1.0 or 0 as for homogeneous lines (Tables 4, 6, 7, 8, and 9). This adjusts the allele frequency data for the purposes of calculating the probability of inheriting an allele from an ancestor or for calculating the frequency of an allele within the elite population.

RAPD probes typically identify dominant markers, i.e., at any locus, only one allele is represented by a band, while "another allele" is evidenced by the absence of the band. If the allele identified by the dominant band is present, there is no easy way to tell if other alleles are present in a DNA sample. However, when working with inbred lines, most of the loci are homozygous and homogeneous. It is, therefore, safe to assume that presence of the band indicates homozygosity for one allele and absence of the band indicates homozygosity for another allele. This was the predominant case in Applicants' soybean survey. Individual RAPD probes identified from one to three polymorphic bands that represent the dominant marker at from one to three loci, respectively. Based on mutual exclusivity of bands, two of the RAPD probes (AP3C and AP5B) appeared to identify codominant alleles. For example, band AP3C.1 was usually mutually exclusive to band AP3C.2 and band AP5B.1 was always mutually exclusive to AP5B.2. Hence, bands AP3C.1 and AP3C.2 identify codominant alleles at the AP3C-A locus. Likewise, AP5B.1 and AP5B.2 identify codominant alleles at the AP5B-A locus. AP5B also identified band AP5B.3 which appears to be independent of bands AP5B.1 and AP5B.2 and, therefore, diagnostic of a different locus (named the AP5B-B locus).

For loci defined by dominant markers, alleles represented by missing bands were given an allele designation that included the word "NOT" to indicate which allele was "not present". For example, an allele designation of "AP6.2NOT" indicates that some other allele besides AP6.2 is present. "AP6.2NOT" was a more accurate designation than "AP6.3" since only AP6.2 could be positively identified.

TABLE 4A

MARKER GENOTYPES OF ANCESTRAL SOYBEAN LINES

| PROBE | ENZYME | LOCUS | BAND (ALLELE) | CNS | MAND | MACH | S100 | RICH | ROAN | AK | S171 | TOKY | PI54 | MUKD |
|---|---|---|---|---|---|---|---|---|---|---|---|---|---|---|
| | | | | | | | | allele frequency within line | | | | | | |
| 1148 | E1 | 1148-A | 1148.0 | 1 | 1 | 0 | 1 | 0 | 1 | 1 | 0 | 1 | 0 | 0 |
| 1148 | E1 | 1148-A | 1148.2 | 0 | 0 | 1 | 0 | 1 | 0 | 0 | 1 | 0 | 1 | 1 |
| 1159 | E5 | 1159-A | 1159.0 | 1 | 0 | 1 | 0 | 1 | 1 | 0 | 0 | 0 | 0 | 0 |
| 1159 | E5 | 1159-A | 1159.2 | 0 | 1 | 0 | 1 | 0 | 0 | 1 | 1 | 1 | 1 | 1 |
| 1202 | E1 | 1202-A | 1202.0 | 0 | 0 | 0 | 1 | 0 | 1 | 0 | 0 | 0 | 0 | 0 |
| 1202 | E1 | 1202-A | 1202.2 | 1 | 0 | 1 | 0 | 0 | 0 | 0 | 1 | 1 | 1 | 1 |
| 1202 | E1 | 1202-A | 1202.3 | 0 | 1 | 0 | 0 | 1 | 0 | 1 | 0 | 0 | 0 | 0 |
| 1203 | H3 | 1203-A | 1203.2 | 1 | 0 | 0 | 1 | 0 | 1 | 1 | 0 | 1 | 0 | 1 |
| 1203 | H3 | 1203-A | 1203.2 | 0 | 1 | 1 | 0 | 1 | 0 | 0 | 1 | 0 | 1 | 0 |
| 1318 | E5 | 1318-A | 1318.0 | 1 | 0 | 1 | 0 | 1 | 1 | 0 | 0 | 0 | 0 | 0 |
| 1318 | E5 | 1318-A | 1318.2 | 0 | 1 | 0 | 1 | 0 | 0 | 1 | 0 | 1 | 1 | 1 |
| 1318 | E5 | 1318-B | 1318.3 | 0 | 0 | 0 | 0 | 0 | 0 | 0 | 1 | 0 | 0 | 0 |
| 1318 | E5 | 1318-B | 1318.4 | 1 | 1 | 1 | 1 | 1 | 1 | 1 | 0 | 1 | 1 | 1 |
| 1329 | E1 | 1329-A | 1329.0 | 1 | 0 | 1 | 0 | 1 | 1 | 0 | 0 | 0 | 0 | 0 |
| 1329 | E1 | 1329-A | 1329.2 | 0 | 1 | 0 | 1 | 0 | 0 | 1 | 1 | 1 | 1 | 1 |
| 1342 | E1 | 1342-A | 1342.2 | 1 | 0 | 1 | 0 | 1 | 1 | 0 | 0 | 1 | 0 | 0 |
| 1342 | E1 | 1342-A | 1342.2 | 0 | 1 | 0 | 1 | 0 | 0 | 1 | 1 | 0 | 1 | 1 |
| 1409 | H3 | 1409-A | 1409.0 | 1 | 0 | 0 | 0 | 0 | 1 | 0 | 0 | 0 | 0 | 0 |
| 1409 | H3 | 1409-A | 1409.2 | 0 | 1 | 1 | 1 | 1 | 0 | 1 | 1 | 1 | 1 | 1 |
| 1443 | E5 | 1443-A | 1443.0 | 1 | 0 | 0 | 1 | 0 | 1 | 1 | 0 | 1 | 0 | 0 |
| 1443 | E5 | 1443-A | 1443.2 | 0 | 1 | 1 | 0 | 1 | 0 | 0 | 1 | 0 | 1 | 1 |
| 1450 | E5 | 1450-A | 1450.0 | 1 | 1 | 1 | 1 | 1 | 1 | 0 | 1 | 1 | 1 | 1 |
| 1450 | E5 | 1450-A | 1450.2 | 0 | 0 | 0 | 0 | 0 | 0 | 1 | 0 | 0 | 0 | 0 |
| 1487 | H3 | 1487-A | 1487.0 | 0 | 0 | 0 | 0 | 0 | 0 | 0 | 0 | 0 | 0 | 0 |
| 1487 | H3 | 1487-A | 1487.2 | 1 | 1 | 1 | 1 | 1 | 1 | 1 | 1 | 1 | 1 | 1 |
| 1492 | H3 | 1492-A | 1492.1 | 1 | 1 | 1 | 0 | 1 | 1 | 1 | 0 | 1 | 0 | 0 |
| 1492 | H3 | 1492-A | 1492.2 | 0 | 0 | 0 | 1 | 0 | 0 | 0 | 1 | 0 | 1 | 1 |
| 1503 | E5 | 1503-A | 1503.0 | 0 | 0 | 0 | 1 | 0 | 0 | 0 | 0 | 0 | 0 | 0 |
| 1503 | E5 | 1503-A | 1503.2 | 1 | 1 | 1 | 0 | 1 | 1 | 1 | 1 | 1 | 1 | 1 |
| 1522 | H3 | 1522-A | 1522.0 | 0 | 1 | 1 | 0 | 1 | 0 | 0 | 1 | 0 | 1 | 1 |
| 1522 | H3 | 1522-A | 1522.2 | 1 | 0 | 0 | 1 | 0 | 1 | 1 | 0 | 1 | 0 | 0 |
| 1525 | E5 | 1525-A | 1525.0 | 0 | 0 | 0 | 0 | 0 | 0 | 0 | 0 | 0 | 0 | 0 |
| 1525 | H3 | 1525-A | 1525.2 | 1 | 1 | 1 | 1 | 1 | 1 | 1 | 1 | 1 | 1 | 1 |
| 1529 | H3 | 1529-A | 1529.0 | 1 | 1 | 1 | 1 | 0 | 1 | 1 | 0 | 1 | 0 | 0 |
| 1529 | H3 | 1529-A | 1529.2 | 0 | 0 | 0 | 0 | 1 | 0 | 0 | 1 | 0 | 1 | 1 |
| 1587 | E5 | 1587-A | 1587.0 | 1 | 1 | 1 | 0 | 1 | 1 | 1 | 0 | 1 | 0 | 0 |
| 1593 | E5 | 1593-A | 1593.0 | 0 | 0 | 1 | 0 | 1 | 1 | 0 | 0 | 1 | 0 | 0 |
| 1593 | E5 | 1593-A | 1593.2 | 1 | 1 | 0 | 1 | 0 | 0 | 1 | 1 | 0 | 1 | 1 |
| 1596 | E5 | 1596-A | 1596.0 | 0 | 1 | 0 | 0 | 0 | 1 | 0 | 0 | 0 | 0 | 0 |
| 1596 | E5 | 1596-A | 1596.2 | 1 | 0 | 1 | 1 | 1 | 0 | 1 | 1 | 1 | 1 | 1 |
| 1596 | E5 | 1596-A | 1596.3 | 0 | 0 | 0 | 0 | 0 | 0 | 0 | 0 | 0 | 0 | 0 |
| 1610 | E1 | 1610-A | 1610.0 | 0 | 0 | 1 | 1 | 1 | 0 | 0 | 0 | 0 | 0 | 1 |
| 1610 | E1 | 1610-A | 1610.2 | 1 | 1 | 0 | 0 | 0 | 1 | 1 | 1 | 1 | 1 | 0 |
| AP3C | | AP3C-A | AP3C.1 | 0 | 1 | 1 | 0 | 0 | 0 | 0 | 1 | 0 | 1 | 1 |
| AP3C | | AP3C-A | AP3C.2 | 1 | 0 | 0 | 1 | 1 | 1 | 1 | 0 | 1 | 0 | 1 |
| AP4C | | AP4C-A | AP4C.1 | 0 | 0 | 0 | 0 | 0 | 0 | 0 | 1 | 0 | 0 | 0 |

TABLE 4A-continued

MARKER GENOTYPES OF ANCESTRAL SOYBEAN LINES

| PROBE | ENZYME | LOCUS | BAND (ALLELE) | CNS | MAND | MACH | S100 | RICH | ROAN | AK | SI71 | TOKY | PI54 | MUKD |
|---|---|---|---|---|---|---|---|---|---|---|---|---|---|---|
| AP4C | | AP4C-A | AP4C.1NOT | 1 | 1 | 1 | 1 | 1 | 1 | 1 | 0 | 0 | 1 | 1 |
| AP4C | | AP4C-B | AP4C.2 | 0 | 0 | 0 | 1 | 0 | 1 | 1 | 1 | 1 | 1 | 1 |
| AP4C | | AP4C-B | AP4C.2NOT | 1 | 1 | 1 | 0 | 1 | 0 | 0 | 0 | 0 | 0 | 0 |
| AP4C | | AP4C-C | AP4C.3 | 1 | 1 | 0 | 0 | 0 | 0 | 0 | 1 | 1 | 0 | 1 |
| AP4C | | AP4C-C | AP4C.3NOT | 0 | 0 | 1 | 1 | 1 | 1 | 1 | 0 | 0 | 1 | 0 |
| AP5 | | AP5-A | AP5.1 | 1 | 0 | 0 | 1 | 0 | 1 | 0 | 1 | 1 | 0 | 0 |
| AP5 | | AP5-A | AP5.1NOT | 0 | 1 | 1 | 0 | 1 | 0 | 1 | 0 | 0 | 1 | 1 |
| AP5 | | AP5-B | AP5.2 | 0 | 0 | 0 | 0 | 0 | 0 | 1 | 1 | 1 | 0 | 0 |
| AP5 | | AP5-B | AP5.2NOT | 1 | 1 | 1 | 1 | 1 | 1 | 0 | 0 | 0 | 1 | 1 |
| AP5 | | AP5-C | AP5.3 | 1 | 1 | 1 | 1 | 1 | 1 | 0 | 0 | 0 | 0 | 0 |
| AP5 | | AP5-C | AP5.3NOT | 0 | 0 | 0 | 0 | 0 | 0 | 1 | 1 | 1 | 1 | 1 |
| AP5B | | AP5B-A | AP5B.1 | 0 | 0 | 0 | 0 | 0 | 0 | 1 | 0 | 0 | 0 | 0 |
| AP5B | | AP5B-A | AP5B.2 | 1 | 1 | 1 | 1 | 1 | 1 | 0 | 1 | 1 | 1 | 1 |
| AP5B | | AP5B-B | AP5B.3 | 1 | 0 | 0 | 0 | 0 | 0 | 1 | 0 | 0 | 0 | 1 |
| AP5B | | AP5B-B | AP5B.3NOT | 0 | 1 | 1 | 1 | 1 | 1 | 0 | 1 | 1 | 1 | 0 |
| AP5C | | AP5C-A | AP5C.1 | 1 | 0 | 0 | 1 | 0 | 0 | 1 | 0 | 0 | 0 | 0 |
| AP5C | | AP5C-A | AP5C.1NOT | 0 | 1 | 1 | 0 | 1 | 1 | 0 | 1 | 1 | 1 | 1 |
| AP5C | | AP5C-B | AP5C.2 | 0 | 0 | 1 | 0 | 1 | 0 | 0 | 1 | 1 | 0 | 0 |
| AP5C | | AP5C-B | AP5C.2NOT | 1 | 1 | 0 | 1 | 0 | 1 | 1 | 0 | 0 | 1 | 1 |
| AP5C | | AP5C-C | AP5C.3 | 1 | 1 | 0 | 1 | 0 | 1 | 1 | 0 | 0 | 1 | 0 |
| AP5C | | AP5C-C | AP5C.3NOT | 0 | 0 | 1 | 0 | 1 | 0 | 0 | 1 | 1 | 0 | 1 |
| AP5G | | AP5G-A | AP5G.1 | 0 | 1 | 0 | 1 | 0 | | 0 | 0 | 0 | 0 | 0 |
| AP5G | | AP5G-A | AP5G.1NOT | 1 | 0 | 1 | 0 | 1 | | 1 | 1 | 1 | 1 | 1 |
| AP5G | | AP5G-B | AP5G.2 | 0 | 0 | 1 | 0 | 0 | | 1 | 0 | 0 | 1 | 1 |
| AP5G | | AP5G-B | AP5G.2NOT | 1 | 1 | 0 | 1 | 1 | | 0 | 1 | 1 | 0 | 0 |
| AP5H | | AP5H-A | AP5H.1 | 1 | 1 | 0 | 0 | 0 | 1 | 0 | 0 | 0 | 1 | 1 |
| AP5H | | AP5H-A | AP5H.1NOT | 0 | 0 | 1 | 1 | 1 | 0 | 1 | 1 | 1 | 0 | 0 |
| AP6 | | AP6-A | AP6.2 | 0 | 0 | 1 | 0 | 1 | | 1 | 1 | 1 | 1 | 1 |
| AP6 | | AP6-A | AP6.2NOT | 1 | 1 | 0 | 1 | 0 | | 0 | 0 | 0 | 0 | 0 |
| AP7 | | AP7-A | AP7.1 | 0 | 1 | 0 | 1 | 0 | 0 | 0 | 0 | 0 | 1 | 0 |
| AP7 | | AP7-A | AP7.1NOT | 1 | 0 | 1 | 0 | 1 | 1 | 1 | 1 | 1 | 0 | 1 |
| AP7 | | AP7-B | AP7.2 | 1 | 0 | 1 | 0 | 1 | 1 | 1 | 0 | 1 | 1 | 1 |
| AP7 | | AP7-B | AP7.2NOT | 0 | 1 | 0 | 1 | 0 | 0 | 0 | 1 | 0 | 0 | 0 |
| AP8B | | AP8B-A | AP8B.1 | 1 | 0 | 0 | 0 | 0 | 1 | 1 | 1 | 1 | 1 | 1 |
| AP8B | | AP8B-A | AP8B.1NOT | 0 | 1 | 1 | 1 | 1 | 0 | 0 | 0 | 0 | 0 | 0 |
| AP8B | | AP8B-B | AP8B.2 | 0 | 0 | 1 | 0 | 0 | 0 | 0 | 1 | 1 | 0 | 0 |
| AP8B | | AP8B-B | AP8B.2NOT | 1 | 1 | 0 | 1 | 1 | 1 | 1 | 0 | 0 | 1 | 1 |
| AP8B | | AP8B-C | AP8B.3 | 0 | 1 | 0 | 0 | 0 | 0 | 0 | 0 | 0 | 0 | 1 |
| AP8B | | AP8B-C | AP8B.3NOT | 1 | 0 | 1 | 1 | 1 | 1 | 1 | 1 | 1 | 1 | 0 |
| AP8F | | AP8F-A | AP8F.1 | 0 | 0 | 1 | 0 | 1 | 1 | 1 | 0 | 1 | 1 | 1 |
| AP8F | | AP8F-A | AP8F.1NOT | 1 | 1 | 0 | 1 | 0 | 0 | 0 | 1 | 0 | 0 | 0 |
| AP8H | | AP8H-A | AP8H.1 | 1 | 1 | 1 | 0 | 1 | 1 | 1 | 1 | 1 | 1 | 1 |
| AP8H | | AP8H-A | AP8H.1NOT | 0 | 0 | 0 | 1 | 0 | 0 | 0 | 0 | 0 | 0 | 0 |
| AP8H | | AP8H-B | AP8H.2 | 1 | 1 | 1 | 1 | 1 | 1 | 1 | 1 | 1 | 1 | 1 |
| AP8H | | AP8H-B | AP8H.2NOT | 0 | 0 | 0 | 0 | 0 | 0 | 0 | 0 | 0 | 0 | 0 |

TABLE 4B

MARKER GENOTYPES OF ELITE SOYBEAN LINES

| PROBE | ENZYME | LOCUS | BAND (ALLELE) | 1939 | 3127 | 3205 | 3307 | WM82 | 3966 | 4271 | 4595 | 4906 | 4997 | 5474 | ESEX |
|---|---|---|---|---|---|---|---|---|---|---|---|---|---|---|---|
| | | | | | | | | allele frequency within line | | | | | | | |
| 1148 | E1 | 1148-A | 1148.0 | .5 | 0 | 0 | 0 | 0 | .5 | .5 | 0 | 1 | 1 | 1 | 1 |
| 1148 | E1 | 1148-A | 1148.2 | .5 | 1 | 1 | 1 | 1 | .5 | .5 | 1 | 0 | 0 | 0 | 0 |
| 1159 | E5 | 1159-A | 1159.0 | 1 | 1 | 1 | 0 | 1 | 1 | 1 | 1 | 1 | 1 | 1 | 1 |
| 1159 | E5 | 1159-A | 1159.2 | 0 | 0 | 0 | 1 | 0 | 0 | 0 | 0 | 0 | 0 | 0 | 0 |
| 1202 | E1 | 1202-A | 1202.0 | 1 | 0 | 0 | .5 | 1 | 0 | 0 | 0 | 0 | 0 | 0 | 0 |
| 1202 | E1 | 1202-A | 1202.2 | 0 | 1 | 1 | .5 | 0 | 1 | 1 | 1 | 1 | 1 | 1 | 1 |
| 1202 | E1 | 1202-A | 1202.3 | 0 | 0 | 0 | 0 | 0 | 0 | 0 | 0 | 0 | 0 | 0 | 0 |
| 1203 | H3 | 1203-A | 1203.0 | 0 | 1 | 1 | .5 | 0 | .5 | .5 | 0 | 1 | 1 | 1 | 1 |
| 1203 | H3 | 1203-A | 1203.2 | 1 | 0 | 0 | .5 | 1 | .5 | .5 | 1 | 0 | 0 | 0 | 0 |
| 1318 | E5 | 1318-A | 1318.0 | 0 | 1 | 0 | 1 | 0 | 1 | 0 | 0 | 1 | 0 | 1 | 1 |
| 1318 | E5 | 1318-A | 1318.2 | 1 | 0 | 1 | 0 | 1 | 0 | 1 | 1 | 0 | 1 | 0 | 0 |
| 1318 | E5 | 1318-B | 1318.3 | 0 | 0 | 0 | 0 | 0 | 0 | 0 | 0 | 0 | 0 | 0 | 0 |
| 1318 | E5 | 1318-B | 1318.4 | 1 | 1 | 1 | 1 | 1 | 1 | 1 | 1 | 1 | 1 | 1 | 1 |
| 1329 | E1 | 1329-A | 1329.0 | 1 | 1 | 1 | 1 | 1 | 1 | 1 | 1 | 1 | 1 | 0 | 1 |
| 1329 | E1 | 1329-A | 1329.2 | 0 | 0 | 0 | 0 | 0 | 0 | 0 | 0 | 0 | 0 | 1 | 0 |
| 1342 | E1 | 1342-A | 1342.0 | 0 | 0 | 0 | 0 | 0 | 1 | 0 | 1 | 0 | 0 | 1 | 1 |
| 1342 | E1 | 1342-A | 1342.2 | 1 | 1 | 1 | 1 | 1 | 0 | 1 | 0 | 1 | 1 | 0 | 0 |
| 1409 | H3 | 1409-A | 1409.0 | 1 | 0 | 0 | 0 | 0 | 0 | 0 | 0 | 0 | 0 | 0 | 0 |
| 1409 | H3 | 1409-A | 1409.2 | 0 | 1 | 1 | 1 | 1 | 1 | 1 | 1 | 1 | 1 | 1 | 1 |
| 1443 | E5 | 1443-A | 1443.0 | 1 | 1 | 1 | 1 | 1 | 1 | 1 | 1 | 0 | 0 | 0 | 1 |
| 1443 | E5 | 1443-A | 1443.2 | 0 | 0 | 0 | 0 | 0 | 0 | 0 | 0 | 1 | 1 | 1 | 0 |
| 1450 | E5 | 1450-A | 1450.0 | 0 | 0 | 0 | 0 | 0 | 0 | 0 | 0 | 1 | 1 | 0 | 0 |
| 1450 | E5 | 1450-A | 1450.2 | 1 | 1 | 1 | 1 | 1 | 1 | 1 | 1 | 0 | 0 | 1 | 1 |
| 1487 | H3 | 1487-A | 1487.0 | 0 | 0 | 0 | 0 | 0 | 0 | 0 | 1 | 0 | 0 | 1 | 0 |
| 1487 | H3 | 1487-A | 1487.2 | 1 | 1 | 1 | 1 | 1 | 1 | 1 | 0 | 1 | 1 | 0 | 1 |
| 1492 | H3 | 1492-A | 1492.0 | 0 | 1 | 0 | 1 | 0 | .5 | 0 | 1 | 1 | 1 | 0 | 1 |
| 1492 | H3 | 1492-A | 1492.2 | 1 | 0 | 1 | 0 | 1 | .5 | 1 | 0 | 0 | 0 | 1 | 0 |
| 1503 | E5 | 1503-A | 1503.0 | 1 | 1 | 1 | 0 | 1 | 1 | 1 | 1 | 1 | 1 | 1 | 1 |
| 1503 | E5 | 1503-A | 1503.2 | 0 | 0 | 0 | 1 | 0 | 0 | 0 | 0 | 0 | 0 | 0 | 0 |
| 1522 | H3 | 1522-A | 1522.0 | 0 | 0 | 0 | 0 | 1 | 1 | 0 | 1 | 0 | 0 | 1 | 0 |
| 1522 | H3 | 1522-A | 1522.2 | 1 | 1 | 1 | 1 | 0 | 0 | 1 | 0 | 1 | 1 | 0 | 1 |
| 1525 | H3 | 1525-A | 1525.0 | 0 | 0 | 0 | 0 | 0 | 0 | 0 | 0 | 0 | 0 | 0 | 0 |
| 1525 | H3 | 1525-A | 1525.2 | 1 | 1 | 1 | 1 | 1 | 1 | 1 | 1 | 1 | 1 | 1 | 1 |
| 1529 | E1 | 1529-A | 1529.0 | 0 | 0 | 0 | 0 | 0 | 0 | 0 | 0 | 0 | 0 | .5 | 0 |
| 1529 | E1 | 1529-A | 1529.2 | 1 | 1 | 1 | 1 | 1 | 1 | 1 | 1 | 1 | 1 | .5 | 1 |
| 1587 | E5 | 1587-A | 1587.0 | 1 | 1 | 1 | 1 | 1 | 1 | 1 | 1 | 0 | 0 | 1 | 0 |
| 1587 | E5 | 1587-A | 1587.2 | 0 | 0 | 0 | 0 | 0 | 0 | 0 | 0 | 1 | 1 | 0 | 1 |
| 1593 | E5 | 1593-A | 1593.0 | 0 | | 1 | 1 | 1 | 1 | 1 | 1 | 0 | 0 | 0 | 1 |
| 1593 | E5 | 1593-A | 1593.2 | 1 | | 0 | 0 | 0 | 0 | 0 | 0 | 1 | 1 | 1 | 0 |
| 1596 | E5 | 1596-A | 1596.0 | 1 | 1 | 1 | 0 | 0 | 1 | 1 | 0 | 1 | 1 | 1 | 1 |
| 1596 | E5 | 1596-A | 1596.2 | 0 | 0 | 0 | 0 | 1 | 0 | 0 | 1 | 0 | 0 | 0 | 0 |
| 1596 | E5 | 1596-A | 1596.3 | 0 | 0 | 0 | 1 | 0 | 0 | 0 | 0 | 0 | 0 | 0 | 0 |
| 1610 | E1 | 1610-A | 1610.0 | 0 | 1 | 0 | 1 | 1 | 1 | 1 | 1 | 1 | 1 | 1 | 1 |
| 1610 | E1 | 1610-A | 1610.2 | 1 | 0 | 1 | 0 | 0 | 0 | 0 | 0 | 0 | 0 | 0 | 0 |
| AP3C | | AP3C-A | AP3C.1 | 1 | 0 | 1 | 0 | 0 | | 0 | 0 | | 0 | 0 | 0 |
| AP3C | | AP3C-A | AP3C.2 | 0 | 1 | 0 | 1 | 1 | | 1 | 1 | | 1 | 1 | 1 |
| AP4C | | AP4C-A | AP4C.1 | 0 | 0 | 0 | 0 | 0 | 0 | 0 | 0 | | 0 | 0 | 0 |
| AP4C | | AP4C-A | AP4C.1NOT | 1 | 1 | 1 | 1 | 1 | 1 | 1 | 1 | | 1 | 1 | 1 |
| AP4C | | AP4C-B | AP4C.2 | 1 | 1 | 1 | 1 | 1 | 1 | 1 | 1 | | 1 | 1 | 1 |
| AP4C | | AP4C-B | AP4C.2NOT | 0 | 0 | 0 | 0 | 0 | 0 | 0 | 0 | | 0 | 0 | 0 |
| AP4C | | AP4C-C | AP4C.3 | 1 | 1 | 1 | 1 | 0 | 1 | 1 | 1 | | 1 | 1 | 1 |
| AP4C | | AP4C-C | AP4C.3NOT | 0 | 0 | 0 | 0 | 1 | 0 | 0 | 0 | | 0 | 0 | 0 |
| AP5 | | AP5-A | AP5.1 | 1 | 1 | 1 | 1 | 1 | 1 | 1 | 0 | | 1 | 1 | 0 |
| AP5 | | AP5-A | AP5.1NOT | 0 | 0 | 0 | 0 | 0 | 0 | 0 | 1 | | 0 | 0 | 1 |
| AP5 | | AP5-B | AP5.2 | 0 | 0 | 0 | 1 | 1 | 1 | 1 | 1 | | 0 | 0 | 0 |
| AP5 | | AP5-B | AP5.2NOT | 1 | 1 | 1 | 0 | 0 | 0 | 0 | 0 | | 1 | 1 | 1 |
| AP5 | | AP5-C | AP5.3 | 1 | 1 | 1 | 0 | 0 | 0 | 0 | 1 | | 1 | 0 | 1 |
| AP5 | | AP5-C | AP5.3NOT | 0 | 0 | 0 | 0 | 1 | 1 | 1 | 0 | | 0 | 1 | 0 |
| AP5B | | AP5B-A | AP5B.1 | 1 | 1 | 1 | 1 | 1 | 1 | 1 | 1 | | 1 | 0 | 0 |
| AP5B | | AP5B-A | AP5B.2 | 0 | 0 | 0 | 0 | 0 | 0 | 0 | 0 | | 0 | 1 | 1 |
| AP5B | | AP5B-B | AP5B.3 | 1 | 1 | 1 | 1 | 0 | 1 | 1 | 1 | | 1 | 1 | 1 |
| AP5B | | AP5B-B | AP5B.3NOT | 0 | 0 | 0 | 0 | 1 | 0 | 0 | 0 | | 0 | 0 | 0 |
| AP5C | | AP5C-A | AP5C.1 | 1 | 1 | 1 | 1 | 1 | 1 | 1 | 1 | | 1 | 1 | 1 |
| AP5C | | AP5C-A | AP5C.1NOT | 0 | 0 | 0 | 0 | 0 | 0 | 0 | | 0 | 0 | 0 | |
| AP5C | | AP5C-B | AP5C.2 | 1 | 1 | 1 | 1 | 1 | 1 | 1 | 1 | | 1 | 1 | 1 |
| AP5C | | AP5C-B | AP5C.2NOT | 0 | 0 | 0 | 0 | 0 | 0 | 0 | 0 | | 0 | 0 | 0 |
| AP5C | | AP5C-C | AP5C.3 | 1 | 1 | 1 | 1 | 1 | 1 | 1 | 1 | | 1 | 1 | 1 |
| AP5C | | AP5C-C | AP5C.3NOT | 0 | 0 | 0 | 0 | 0 | 0 | 0 | 0 | | 0 | 0 | 0 |
| AP5G | | AP5G-A | AP5G.1 | 0 | 0 | 0 | 0 | 0 | 0 | 0 | 0 | | 1 | 0 | 0 |
| AP5G | | AP5G-A | AP5G.1NOT | 1 | 1 | 1 | 1 | 1 | 1 | 1 | 1 | | 0 | 1 | 1 |
| AP5G | | AP5G-B | AP5G.2 | 1 | 0 | 0 | 0 | 1 | 0 | 1 | 0 | | 0 | 0 | 0 |
| AP5G | | AP5G-B | AP5G.2NOT | 0 | 1 | 1 | 1 | 0 | 1 | 0 | 1 | | 1 | 1 | 1 |
| AP5H | | AP5H-A | AP5H.1 | 0 | 1 | 0 | 1 | 1 | 1 | 0 | 1 | | 1 | 1 | 1 |
| AP5H | | AP5H-A | AP5H.1NOT | 1 | 0 | 1 | 0 | 0 | 0 | 1 | 0 | | 0 | 0 | 0 |
| AP6 | | AP6-A | AP6.2 | 0 | 0 | 1 | 0 | 0 | 0 | 0 | 0 | | 0 | 0 | 0 |
| AP6 | | AP6-A | AP6.2NOT | 1 | 1 | 0 | 1 | 1 | 1 | 1 | 1 | | 1 | 1 | 1 |
| AP7 | | AP7-A | AP7.1 | 0 | 0 | 0 | 0 | 1 | 0 | 0 | 0 | | 0 | 0 | 0 |

TABLE 4B-continued

| | | | MARKER GENOTYPES OF ELITE SOYBEAN LINES | | | | | | | | | | | |
|---|---|---|---|---|---|---|---|---|---|---|---|---|---|---|
| PROBE | ENZYME | LOCUS | BAND (ALLELE) | 1939 | 3127 | 3205 | 3307 | WM82 | 3966 | 4271 | 4595 | 4906 | 4997 | 5474 | ESEX |
| AP7 | | AP7-A | AP7.1NOT | 1 | 1 | 1 | 1 | 0 | 1 | 1 | 1 | | 1 | 1 | 1 |
| AP7 | | AP7-B | AP7.2 | | | 0 | 1 | 1 | | | 1 | | 0 | 0 | 0 |
| AP7 | | AP7-B | AP7.2NOT1 | | | 1 | 0 | 0 | | | 0 | | 1 | 1 | 1 |
| AP8B | | AP8B-A | AP8B.1 | 1 | 1 | 0 | 1 | 1 | 1 | 0 | 1 | | 0 | 0 | 0 |
| AP8B | | AP8B.1-NOT | 0 | 0 | 1 | 0 | 0 | 0 | 1 | 0 | | 1 | 1 | 1 | |
| AP8B | | AP8B-B | AP8B.2 | 1 | 1 | 1 | 0 | 1 | 1 | 1 | 1 | | 1 | 1 | 1 |
| AP8B | | AP8B-B | AP8B.2NOT | 0 | 0 | 0 | 1 | 0 | 0 | 0 | 0 | | 0 | 0 | 0 |
| AP8B | | AP8B-C | AP8B.3 | 0 | 0 | 0 | 0 | 0 | 0 | 0 | 0 | | 0 | 1 | 0 |
| AP8B | | AP8B-C | AP8B.3NOT | 1 | 1 | 1 | 1 | 1 | 1 | 1 | 1 | | 1 | 0 | 1 |
| AP8F | | AP8F-A | AP8F.1 | 0 | 0 | 0 | 0 | 0 | 0 | 0 | 1 | | 0 | 0 | 1 |
| AP8F | | AP8F-A | AP8F.1NOT | 1 | 1 | 1 | 1 | 1 | 1 | 1 | 0 | | 1 | 1 | 0 |
| AP8H | | AP8H-A | AP8H.1 | 0 | 0 | 0 | 0 | 0 | 0 | 0 | 0 | | 0 | 0 | 0 |
| AP8H | | AP8H-A | AP8H.1NOT | 1 | 1 | 1 | 1 | 1 | 1 | 1 | 1 | | 1 | 1 | 1 |
| AP8H | | AP8H-B | AP8H.2 | 1 | 1 | 0 | 1 | 1 | 1 | 1 | 1 | | 1 | 1 | 1 |
| AP8H | | AP8H-B | AP8H.2NOT | 0 | 0 | 1 | 0 | 0 | 0 | 0 | 0 | | 0 | 0 | 0 |

Calculating the Probability of Inheriting Each Allele in Each Elite Line

After determination of molecular marker genotype, lines were grouped into two populations (elite and ancestral) for the purpose of calculating the average probability of inheriting each allele assuming no affect of selection. This average probability serves as the expected allele frequency within the elite population for the purpose of hypothesis testing. Expected allele frequency was obtained by averaging the individual probabilities of inheriting an allele over all 12 elite lines.

For example, given the pedigree of elite line $E_i$ (FIG. 2), it was assumed that the $A_i$ were mostly homozygous, and that at each cross in the pedigree, the $F_1$ was selfed several times so that each node in the pedigree was also mostly homozygous, including the final product, $E_i$.

At several loci (assumed independent, i.e., not linked), genotype is characterized by a marker (Equation 1):

$$M_{1,j} = \begin{matrix} 1 \\ 0.5 \\ 0 \end{matrix} \qquad 1$$

The "1" indicates presence of the allele, i.e., a specific marker phenotype allele, "0.5" indicates that the line is segregating for the allele (in cases of codominant markers such as RFLP's), and "0" indicates absence of the allele. $M_{l,j}$ is actually the allele frequency within the line. The subscript l indicates locus, and the subscript j indicates an individual line.

From the pedigrees, the coefficient of parentage $C_{j,i}$ of each ancestor, j in each elite, i was calculated (Table 3). The probability of finding an allele at a locus in an elite, under the null hypothesis of no selection during development of the elite was calculated (Equation 2):

$$P_{1,i} = \sum_{j}^{Ancestors} C_{j,i} M_{1,j} \qquad 2$$

Since only the predominant ancestors were included in Applicants' survey, parentage was not completely accounted for. This was reflected in (Equation 3):

$$\sum_{j} C_{j,i} < 1 \qquad 3$$

This was corrected for in an unbiased way by creating a hypothetical parent for each elite with coefficient of parentage (Equation 4):

$$r_i = 1 - \sum_{j} C_{j,i} \qquad 4$$

This was partitioned into two parts, a part that had the band (allele), and a part that did not have the band, in a proportion determined by the fraction of known ancestors that had the band, $f_l$. The summation in Equation 2 was adjusted for missing parentage by adding $r_i f_l$.

In a relatively small number of cases, the presence or absence of the band in an ancestor at a locus was unknown (missing data). In this event, $M_{l,j}$ was substituted with $f_l$.

Calculating the Expected Allele Frequency Within the Elite Population

The probabilities of equation 2 were used to calculate the expected allele frequency $A_l$ (Table 5) at a locus within the elite population, under the null hypothesis that no allele was favored by selection:

$$A_1 = \frac{\sum_{i}^{Elites} P_{1,i}}{n} \qquad 5$$

where n=the number of elite lines with data at said locus. $A_l$ was then converted into the expected count $(x_l)$ of elite lines (Table 5) with a given allele by multiplying $A_l$ by n.

$$x_l = n A_1 \qquad 6$$

Calculating the Observed Allele Frequency Within the Elite Population

The observed allele frequency ($O_l$) for each allele within the elite population was expressed as a count which was the summation of the individual elite allele frequencies:

$$O_1 = \sum_{j}^{Elites} M_{1,j} \qquad 7$$

Comparing Observed Allele Frequency to Expected Allele Frequency

The observed count for each allele among elites ($O_l$) was then compared to the expected count for that allele (Table 5). A chi-square test (Table 5) was used to determine the significance of deviations from expected allele count within each locus:

$$c_1^2 = \Sigma \frac{(O_1 - x_1)^2}{x_1} \text{ (Sum over alleles at a locus)}$$

This statistic should approximate the chi-square distribution where degrees of freedom = number of alleles at the locus − 1. The hypothesis of no selection can be rejected for loci where the upper tail cumulative probability at chi-square is small enough.

TABLE 5

| LOCUS | ALLELE (BAND) | EXPEC FREQ | N | EXPEC COUNT | OBSER COUNT | (o-e) 2/e | chi actuate | LOG PROB | STATUS |
|---|---|---|---|---|---|---|---|---|---|
| 1148-A | 1148.0 | 0.632 | 12 | 7.585 | 5.5 | 0.573 | | | |
| | 1148.2 | 0.368 | 12 | 4.415 | 6.5 | 0.984 | 1.557 | −0.67 | |
| 1159-A | 1159.0 | 0.767 | 12 | 9.199 | 11 | 0.353 | | | |
| | 1159.2 | 0.233 | 12 | 2.801 | 1 | 1.158 | 1.511 | −0.66 | |
| 1202-A | 1202.0 | 0.525 | 12 | 6.301 | 2.5 | 2.293 | | | |
| | 1202.2 | 0.29 | 12 | 3.477 | 9.5 | 10.434 | | | Favorable |
| | 1202.3 | 0.185 | 12 | 2.222 | 0 | 2.222 | 14.949 | −3.25 | |
| 1203-A | 1203.0 | 0.296 | 12 | 3.547 | 7.5 | 4.405 | | | Favorable |
| | 1203.2 | 0.704 | 12 | 8.453 | 4.5 | 1.848 | 6.253 | −1.91 | |
| 1318-A | 1318.0 | 0.703 | 12 | 8.439 | 6 | 0.705 | | | |
| | 1318.2 | 0.297 | 12 | 3.561 | 6 | 1.67 | 2.375 | −0.91 | |
| 1318-B | 1318.3 | 0.149 | 12 | 1.783 | 0 | 1.783 | | | |
| | 1318.4 | 0.851 | 12 | 10.217 | 12 | 0.311 | 2.094 | −0.83 | |
| | | | | | 12 | | | | |
| 1329-A | 1329.0 | 0.616 | 12 | 7.390 | 11 | 1.764 | | | Favorable |
| | 1329.2 | 0.384 | 12 | 4.610 | 1 | 2.827 | 4.591 | −1.49 | |
| 1342-A | 1342.0 | 0.166 | 12 | 1.986 | 4 | 2.042 | | | |
| | 1342.2 | 0.834 | 12 | 10.014 | 8 | 0.405 | 2.447 | −0.93 | |
| 1409-A | 1409.0 | 0.228 | 12 | 2.732 | 1 | 1.098 | | | |
| | 1409.2 | 0.772 | 12 | 9.268 | 11 | 0.324 | 1.422 | −0.63 | |
| 1443-A | 1443.0 | 0.268 | 12 | 3.218 | 9 | 10.388 | | | Favorable |
| | 1443.2 | 0.732 | 12 | 8.782 | 3 | 3.807 | 14.194 | −3.78 | |
| 1450-A | 1450.0 | 0.292 | 12 | 3.500 | 2 | 0.643 | | | |
| | 1450.2 | 0.708 | 12 | 8.500 | 10 | 0.265 | 0.907 | −0.47 | |
| 1487-A | 1487.0 | 0.235 | 12 | 2.816 | 2 | 0.236 | | | |
| | 1487.2 | 0.765 | 12 | 9.184 | 10 | 0.072 | 0.309 | −0.24 | |
| 1492-A | 1492.0 | 0.371 | 12 | 4.449 | 6.5 | 0.946 | | | |
| | 1492.2 | 0.629 | 12 | 7.551 | 5.5 | 0.557 | 1.503 | −0.66 | |
| 1503-A | 1503.0 | 1.000 | 12 | 12.000 | 11 | 0.083 | | | |
| | 1503.2 | 0.000 | 12 | 0.000 | 1 | | 0.083 | −0.11 | |
| 1522-A | 1522.0 | 0.815 | 12 | 9.779 | 4 | 3.415 | | | |
| | 1522.2 | 0.185 | 12 | 2.221 | 8 | 15.038 | 18.453 | −4.76 | Favorable |
| 1525-A | 1525.0 | 0.517 | 12 | 6.202 | 0 | 6.202 | | | |
| | 1525.2 | 0.483 | 12 | 5.798 | 12 | 6.635 | 12.837 | −3.47 | Favorable |
| 1529-A | 1529.0 | 0.367 | 12 | 4.400 | 0.5 | 3.457 | | | Favorable |
| | 1529.2 | 0.633 | 12 | 7.600 | 11.5 | 2.001 | 5.458 | −1.71 | Favorable |
| 1587-A | 1587.0 | 0.481 | 12 | 5.770 | 9 | 1.808 | | | |
| | 1587.2 | 0.519 | 12 | 6.230 | 3 | 1.675 | 3.483 | −1.21 | |
| 1593-A | 1593.0 | 0.849 | 11 | 9.340 | 7 | 0.586 | | | |
| | 1593.2 | 0.151 | 11 | 1.660 | 4 | 3.298 | 3.885 | −1.31 | Favorable |
| 1596-A | 1596.0 | 0.307 | 12 | 3.689 | 9 | 7.647 | | | Favorable |
| | 1596.2 | 0.693 | 12 | 8.311 | 2 | 4.792 | | | |
| | 1596.3 | 0.000 | 12 | 0.000 | 1 | | 12.439 | −2.70 | |
| 1610-A | 1610.0 | 0.752 | 12 | 9.025 | 10 | 0.105 | | | |
| | 1610.2 | 0.248 | 12 | 2.975 | 2 | 0.320 | 0.425 | −0.29 | |
| AP3C-A | AP3C.1 | 0.367 | 10 | 3.672 | 2 | 0.761 | | | |
| | AP3C.2 | 0.710 | 10 | 7.096 | 8 | 0.115 | 0.876 | −0.46 | |
| AP4C-A | AP4C.1 | 0.086 | 11 | 0.943 | 0 | 0.943 | | | |
| | AP4C.1NOT | 0.914 | 11 | 10.057 | 11 | 0.088 | 1.032 | −0.51 | |
| AP4C-B | AP4C.2 | 0.752 | 11 | 8.273 | 11 | 0.899 | | | Favorable |
| | AP4C.2NOT | 0.248 | 11 | 2.727 | 0 | 2.727 | 3.626 | −1.25 | |
| AP4C-C | AP4C.3 | 1.000 | 11 | 11.000 | 10 | 0.091 | | | |
| | AP4C3NOT | 0.000 | 11 | 0.000 | 1 | 0.000 | 0.091 | −0.12 | |
| AP5-A | AP5.1 | 0.831 | 11 | 9.145 | 9 | 0.002 | | | |
| | AP5.1NOT | 0.169 | 11 | 1.855 | 2 | 0.011 | 0.014 | −0.04 | |
| AP5-B | AP5.2 | 0.602 | 11 | 6.620 | 5 | 0.397 | | | |
| | AP5.2NOT | 0.398 | 11 | 4.380 | 6 | 0.599 | 0.996 | −0.50 | |
| AP5-C | AP5.3 | 0.700 | 11 | 7.705 | 7 | 0.065 | | | |
| | AP5.3NOT | 0.300 | 11 | 3.295 | 4 | 0.151 | 0.216 | −0.19 | |
| AP5B-A | AP5B.1 | 0.552 | 11 | 6.077 | 9 | 1.405 | | | Favorable |
| | AP5B.2 | 0.448 | 11 | 4.923 | 2 | 1.735 | 3.141 | −1.12 | |
| AP5B-B | AP5B.3 | 0.849 | 11 | 9.340 | 10 | 0.047 | | | |
| | AP5B.3NOT | 0.151 | 11 | 1.660 | 1 | 0.262 | 0.309 | −0.24 | |
| AP5C-A | AP5C.1 | 0.953 | 11 | 10.485 | 11 | 0.025 | | | |
| | AP5C.1NOT | 0.047 | 11 | 0.515 | 0 | 0.515 | 0.540 | −0.34 | |
| AP5C-B | AP5C.2 | 0.231 | 11 | 2.538 | 11 | 28.220 | | | Favorable |
| | AP5C.2 | 0.769 | 11 | 8.462 | 0 | 8.462 | 36.682 | −8.86 | |
| AP5C-C | AP5C.3 | 0.966 | 11 | 10.623 | 11 | 0.013 | | | |
| | AP5C.3NOT | 0.034 | 11 | 0.377 | 0 | 0.377 | 0.390 | −0.27 | |
| AP5G-A | AP5G.1 | 0.207 | 11 | 2.277 | 1 | 0.716 | | | |

TABLE 5-continued

| LOCUS | ALLELE (BAND) | EXPEC FREQ | N | EXPEC COUNT | OBSER COUNT | (o-e) 2/e | chi actuate | LOG PROB | STATUS |
|---|---|---|---|---|---|---|---|---|---|
| | AP5G.1NOT | 0.793 | 11 | 8.923 | 10 | 0.187 | 0.903 | −0.47 | |
| AP5G-B | AP5G.2 | 0.112 | 11 | 1.234 | 4 | 6.205 | | | Favorable |
| | AP5G.2NOT | 0.888 | 11 | 9.766 | 7 | 0.784 | 6.988 | −2.09 | |
| AP5H-A | AP5H.1 | 0.573 | 11 | 6.300 | 8 | 0.459 | | | |
| | AP5H.1NOT | 0.429 | 11 | 4.700 | 3 | 0.615 | 1.073 | −0.52 | |
| AP6-A | AP6.2 | 0.451 | 11 | 4.961 | 1 | 3.163 | | | |
| | AP6.2NOT | 0.549 | 11 | 6.039 | 10 | 2.599 | 5.762 | −1.79 | Favorable |
| AP7-A | AP7.1 | 0.047 | 11 | 0.515 | 1 | 0.457 | | | |
| | AP7.1NOT | 0.953 | 11 | 10.485 | 10 | 0.022 | 0.479 | −0.31 | |
| AP7-B | AP7.2 | 0.626 | 7 | 4.384 | 3 | 0.437 | | | |
| | AP7.2NOT | 0.374 | 7 | 2.616 | 4 | 0.732 | 1.169 | −0.55 | |
| AP8B-A | AP8B.1 | 0.595 | 11 | 6.548 | 6 | 0.046 | | | |
| | AP8B.1NOT | 0.405 | 11 | 4.452 | 5 | 0.068 | 0.113 | −0.13 | |
| AP8B-B | AP8B.2 | 0.813 | 11 | 8.942 | 10 | 0.125 | | | |
| | AP8B.2NOT | 0.187 | 11 | 2.058 | 1 | 0.544 | 0.669 | −0.38 | |
| AP8B-C | AP8B.3 | 0.319 | 11 | 3.510 | 1 | 1.795 | | | |
| | AP8B.3NOT | 0.681 | 11 | 7.490 | 10 | 0.841 | 2.637 | −0.98 | |
| AP8F-A | AP8F.1 | 0.481 | 11 | 5.287 | 2 | 2.044 | | | |
| | AP8F.1NOT | 0.519 | 11 | 5.713 | 9 | 1.892 | 3.936 | −1.33 | Favorable |
| AP8H-A | AP8H.1 | 0.410 | 11 | 4.513 | 0 | 4.513 | | | |
| | AP8H.1NOT | 0.590 | 11 | 6.487 | 11 | 3.140 | 7.653 | −2.25 | Favorable |
| AP8H-B | AP8H.2 | 0.942 | 11 | 10.367 | 10 | 0.013 | | | |
| | AP8H.2NOT | 0.058 | 11 | 0.633 | 1 | 0.212 | 0.225 | −0.20 | |

Determining which Alleles were Favored by Selection for Agronomics

For each locus, a log probability ("LOG PROB") of −1.0 or less (Table 5) was considered evidence for rejecting the hypothesis that selection did not favor one allele over another. At such loci, the "FAVORABLE ALLELE" was identified as the one that occured more frequently than expected (i.e., had a higher count then expected). Table 6 lists only the favorable alleles identified in Table 5. The alleles are sorted according to the LOG PROB of the chi-square test for their respective loci. Note that although elite lines contain mostly favorable alleles at the loci studied, no one elite line contains all of the favorable alleles (Table 6). The "ideal genotype" at these loci (Table 6) would contain all of the known favorable alleles. It is possible to develop such an ideal genotype by crossing any two lines that complement each other at these loci and then select a segregant that contains only favorable alleles. For example, the breeder could cross lines A1937 and A3205. Progeny from the cross would segregate at the 1202-A, AP5G-B, 1203-A, 1593-A, and AP6-A loci and be fixed for the favorable allele at the other 12 loci listed in Table 6. The breeder could then select only progeny containing the favorable allele at the 5 segregating loci to obtain the ideal genotype listed in Table 6.

The total number of favorable alleles found within a crop species is limited by the thoroughness of the genetic marker survey. It is expected that additional favorable alleles would be identified if more genetic markers and more lines were included in Applicants' soybean survey. This would result in a more complete analysis of the soybean genome.

A distinction between codominant and dominant markers is noteworthy: At loci defined by codominant markers, selection can be based on the presence of the band (or other marker phenotype) that identifies the favorable allele at that locus. However, at loci defined by dominant markers, selection is actually based on the presence of the band (if it identifies a favorable allele) or the absence of the band (if it identifies an unfavorable allele). Hence, selection for "alleles" AP8H.1NOT, AP6.2NOT, or AP8F.1NOT is actually selection against alleles AP8H.1, AP6.2, or AP8F.1, respectively.

TABLE 6

FAVORABLE ALLELE DISTRIBUTION AMONG ELITE LINES

| LOCUS | FAVORABLE ALLELE | LOG PROB | A19 37 | A31 27 | A32 05 | A33 07 | WM 82 | A39 66 | A42 71 | A45 95 | A49 06 | A49 97 | A54 74 | ESEX | IDEAL GENOTYPE |
|---|---|---|---|---|---|---|---|---|---|---|---|---|---|---|---|
| | | | | | | | allele frequency within line | | | | | | | | |
| AP5C-B | AP5C.2 | −8.86 | 1 | 1 | 1 | 1 | 1 | 1 | 1 | 1 | | 1 | 1 | 1 | 1 |
| 1522-A | 1522.2 | −4.76 | 1 | 1 | 1 | 1 | 0 | 0 | 1 | 0 | 1 | 1 | 0 | 1 | 1 |
| 1443-A | 1443.0 | −3.78 | 1 | 1 | 1 | 1 | 1 | 1 | 1 | 1 | 0 | 0 | 0 | 1 | 1 |
| 1525-A | 1525.2 | −3.47 | 1 | 1 | 1 | 1 | 1 | 1 | 1 | 1 | 1 | 1 | 1 | 1 | 1 |
| 1202-A | 1202.2 | −3.25 | 0 | 1 | 1 | .5 | 0 | 1 | 1 | 1 | 1 | 1 | 1 | 1 | 1 |
| 1596-A | 1596.0 | −2.70 | 1 | 1 | 1 | 0 | 0 | 1 | 1 | 0 | 1 | 1 | 1 | 1 | 1 |
| AP5G-B | AP5G.2 | −2.09 | 1 | 0 | 0 | 0 | 1 | 1 | 0 | 1 | 0 | 0 | 0 | 1 | 1 |
| 1203-A | 1203.0 | −1.91 | 0 | 1 | 1 | .5 | 0 | .5 | .5 | 0 | 1 | 1 | 1 | 1 | 1 |
| AP6-A | AP6.2NOT | −1.79 | 1 | 1 | 0 | 1 | 1 | 1 | 1 | 1 | 1 | 1 | 1 | 1 | 1 |
| 1529-A | 1529.2 | −1.71 | 1 | 1 | 1 | 1 | 1 | 1 | 1 | 1 | 1 | 1 | .5 | 1 | 1 |
| 1329-A | 1329.0 | −1.49 | 1 | 1 | 1 | 1 | 1 | 1 | 1 | 1 | 1 | 1 | 0 | 1 | 1 |
| AP8H-A | AP8H.1NOT | −1.33 | 1 | 1 | 1 | 1 | 1 | 1 | 1 | 1 | 1 | 1 | 1 | 1 | 1 |
| AP8F-A | AP8F.1NOT | −1.33 | 1 | 1 | 1 | 1 | 1 | 1 | 1 | 0 | 1 | 1 | 0 | 1 | 1 |
| 1593-A | 1593.2 | −1.31 | 1 | 0 | 0 | 0 | 0 | 0 | 0 | 1 | 1 | 1 | 0 | 1 | 1 |
| AP4C−B | AP4C.2 | −1.25 | 1 | 1 | 1 | 1 | 1 | 1 | 1 | 1 | 1 | 1 | 1 | 1 | 1 |
| 1587-A | 1587.0 | −1.21 | 1 | 1 | 1 | 1 | 1 | 1 | 1 | 1 | 0 | 0 | 1 | 0 | 1 |
| AP5B-A | AP5B.1 | −1.12 | 1 | 1 | 1 | 1 | 1 | 1 | 1 | 1 | 1 | 0 | 0 | 1 | 1 |

EXAMPLE 1A

A Generalized Approach to the Identification of Molecular Markers Associated with Genes Conferring Agronomic Fitness in Soybean Data from Example 1 showing the proportion of elite parentage contributed by major ancestors (Table 3) and the results of the molecular marker survey shown in Tables 4A and 4B were used to demonstrate a more generalized approach to the comparison of observed allele frequency amoung elites, and expected allele frequency based on pedigree analysis.

A More General Approach to the Comparison of the Observed Allele Frequency Among Elites and the Expected Allele Frequency by the Generalized Binomial Distribution It is often the case that the probability of inheriting an allele within each elite pedigree is not the same due to differences in the pedigree structure of each elite line. In such cases, a more appropriate approximation of the probability of inheriting an allele can be obtained as follows. As before, $P_{l,i}$ is the probability of inheriting a specific allele at locus l, for elite i, and the probability of seeing r alleles inherited at locus l, in N trials is calculated as follows:

There are $N!/((N-r)! \cdot r!)$ combinations of elites that have inherited a specific allele r times in N pedigrees. Let $a_{i,k}=1$ only if elite i contributes a specific allele in combination k. The probability of the kth combination is then:

$$\prod_{i=1}^{N} \left\{ \begin{array}{l} P_{1,i} \quad (a_{i,k} = 1) \\ 1 - P_{1,i}, (a_{i,k} \neq 1) \end{array} \right. \qquad 9$$

and the total probability is the sum of the probabilities of all combinations:

$$P(r,N,\vec{p}) = \qquad 10$$

$$\sum_{\substack{\vec{a}=C(k,r,N) \\ k=1,2,\ldots}} \frac{N!}{(N-r)! r!} \prod_{i=1}^{N} \left\{ \begin{array}{l} P_{1,i} \quad (a_{i,k} = 1) \\ 1 - P_{1,i}, (a_{i,k} \neq 1) \end{array} \right.$$

The function C(k,r,N) returns a vector of length N consisting of r "one" elements with the remainder "zero" elements, for the kth combination, and the outer sum indicates an iteration over all possible combinations.

If R specific alleles are observed in N elite pedigrees, and if R is larger than expected, the probability of observing R or more specific alleles inherited in N pedigrees is:

$$\sum_{r=R}^{N} P(r,N,\vec{p}) \qquad 11$$

The analogous equation when R is smaller than expected is:

$$\sum_{r=0}^{R} P(r,N,\vec{p}) \qquad 12$$

If these cumulative probabilities are small enough then the hypothesis that the results happened at random can be rejected, showing evidence for selection at locus 1 for a specific allele in R different pedigrees.

Computation of the General Case

The general case is easily converted into a computer program, and the direct translation works for small problems (N<20) but fails for problems that at first glance might not appear to be significantly larger (e.g. N=50). The computational difficulty comes from a rapid increase in the number of combinations of r as N increases (the worst case is when r=N/2). For example, assume that the product part of Equation 10 can be computed in one microsecond, and that the summation takes negligible time. The computation of a N=20, r=10 case would take 0.185 seconds, N=30, r=15 would take 2.59 minutes, and N=50, r=25 would take 4 years.

One way around this combinatorial problem is to partition the set of probabilities into groups. In the case of relatively shallow pedigrees with few total ancestors, it is likely that the probabilities for a set of N elites will partitoin without approximation into $N_p$ groups, where $N_p<N$. In this case the partitioned problem provides an equivalent but more efficient solution for the general case. If sufficient exact partitioning is not inherent in the set of probabilities, approximate partitioning can be done where nearly equal probabilities are grouped and represented by the average of the members of the group. In this case the partitioned problem provides an approximation to the true solution.

Within each group, probabilities can be computed from the binomial distribution. If a group has $n_g$ members, then the probability of the group inheriting a specific allele $r_g$ times is binomial because each member has the same probability $p_g$, of inheriting the allele. The combinatorial problem is then, given the inheritance of a specific allele r times, how many different ways can these r cases be distributed over the $N_p$ groups, where each group could have inherited a specific allele at most $n_g$ times. A computer program that systematically enumerates the possible arrangements (without duplication) was written. As an example, consider a group of N=24 pedigrees, with the probabilities of inheriting an allele at a locus evenly spaced between 0.1 and 0.9 (24 different values). The results for three levels of partitioning are shown in Table 2.

Application of the General Method to Soybean Example 1

The data presented in Example 1 Tables 3, 4A, and 4B were analysed by this more general method for the comparison of observed and expected allele frequencies amoung elite soybean lines. The results are presented in Table 7. From a comparison of Table 5 and Table 7 it can been seen that the more general approach yields a similar result to that presented in Example 1. This method provides a more generalized approach to the determination of the significance of changes in allele frequency as the result of breeding selection. It also provides a method of determining the probability of inheriting an allele within elite pedigrees that do not contain equivalent pedigree structure. The more generalized method might be utilized when the pedigrees of elite lines comprising an elite population vary greatly in pedigree structure as is the case for corn for example.

TABLE 7

| LOCUS | ALLELE (BAND) | N | EXPEC COUNT | OBSER COUNT | LOG PROB | STATUS |
|---|---|---|---|---|---|---|
| 1148-A | 1148.0 | 9 | 5.90 | 4 | −0.80 | |

TABLE 7-continued

| LOCUS | ALLELE (BAND) | N | EXPEC COUNT | OBSER COUNT | LOG PROB | STATUS |
|---|---|---|---|---|---|---|
| | 1148.2 | 9 | 3.10 | 5 | −0.80 | able |
| 1159-A | 1159.0 | 12 | 9.20 | 11 | −0.72 | |
| | 1159.2 | 12 | 2.80 | 1 | −0.72 | |
| 1202-A | 1202.0 | 11 | 5.80 | 2 | −1.67 | Unfavorable |
| | 1202.2 | 11 | 3.20 | 9 | −3.53 | Favorable |
| | 1202.3 | 12 | 2.20 | 0 | −1.09 | Unfavorable |
| 1203-A | 1203.0 | 9 | 2.60 | 6 | −1.71 | Favorable |
| | 1203.2 | 9 | 6.40 | 3 | −1.71 | |
| 1318-A | 1318.0 | 12 | 8.40 | 6 | −0.95 | |
| | 1318.2 | 12 | 3.60 | 6 | −0.95 | |
| 1318-B | 1318.3 | 12 | 1.80 | 0 | −0.85 | |
| | 1318.4 | 12 | 10.20 | 12 | −0.85 | |
| 1329-A | 1329.0 | 12 | 7.40 | 11 | −1.72 | Favorable |
| | 1329.2 | 12 | 4.60 | 1 | −1.72 | |
| 1342-A | 1342.0 | 12 | 2.00 | 4 | −0.93 | |
| | 1342.2 | 12 | 10.00 | 8 | −0.93 | |
| 1409-A | 1409.0 | 12 | 2.70 | 1 | −0.70 | |
| | 1409.2 | 12 | 9.30 | 11 | −0.70 | |
| 1443-A | 1443.0 | 12 | 3.20 | 9 | −3.35 | Favorable |
| | 1443.2 | 12 | 8.80 | 3 | −3.35 | |
| 1450-A | 1450.0 | 12 | 3.50 | 2 | −0.57 | |
| | 1450.2 | 12 | 8.50 | 10 | −0.57 | |
| 1487-A | 1487.0 | 12 | 2.80 | 2 | −0.36 | |
| | 1487.2 | 12 | 9.20 | 10 | −0.36 | |
| 1492-A | 1492.0 | 11 | 4.10 | 6 | −0.77 | |
| | 1492.2 | 11 | 6.90 | 5 | −0.77 | |
| 1503-A | 1503.0 | 12 | 12.00 | 11 | NaN | |
| | 1503.2 | 12 | 0.00 | 1 | NaN | |
| 1522-A | 1522.0 | 12 | 9.80 | 4 | −3.64 | |
| | 1522.2 | 12 | 2.20 | 8 | −3.64 | Favorable |
| 1525-A | 1525.0 | 12 | 6.20 | 0 | −3.84 | |
| | 1525.2 | 12 | 5.80 | 12 | −3.84 | Favorable |
| 1529-A | 1529.0 | 11 | 4.20 | 0 | −2.34 | |
| | 1529.2 | 11 | 6.80 | 11 | −2.34 | Favorable |
| 1587-A | 1587.0 | 12 | 5.80 | 9 | −1.27 | Favorable |
| | 1587.2 | 12 | 6.20 | 3 | −1.27 | |
| 1593-A | 1593.0 | 11 | 9.40 | 7 | −1.20 | |
| | 1593.2 | 11 | 1.60 | 4 | −1.20 | Favorable |
| 1596-A | 1596.0 | 12 | 3.70 | 9 | −2.94 | Favorable |
| | 1596.2 | 12 | 8.30 | 2 | −3.95 | |
| | 1596.3 | 12 | 0.00 | 1 | NaN | |
| 1610-A | 1610.0 | 12 | 9.00 | 10 | −0.41 | |
| | 1610.2 | 12 | 3.00 | 2 | −0.41 | |
| AP3C-A | AP3C.1 | 10 | 3.80 | 2 | −0.71 | |
| | AP3C.2 | 10 | 7.00 | 8 | −0.42 | |
| AP4C-A | AP4C.1 | 11 | 0.90 | 0 | −0.42 | |
| | AP4C.1 | 11 | 10.10 | 11 | −0.42 | |
| AP4C-B | AP4C.2 | 11 | 8.20 | 11 | −1.49 | Favorable |
| | AP4C.2 | 11 | 2.80 | 0 | −1.49 | |
| AP4C-C | AP4C.3 | 11 | 11.00 | 10 | NaN | |
| | AP4C.3 | 11 | 0.00 | 1 | NaN | |
| AP5-A | AP5.1 | 11 | 9.20 | 9 | −0.24 | |
| | AP5.1 | 11 | 1.80 | 2 | −0.24 | |
| AP5-B | AP5.2 | 11 | 6.60 | 5 | −0.61 | |
| | AP5.2 | 11 | 4.40 | 6 | −0.61 | |
| AP5-C | AP5.3 | 11 | 7.60 | 7 | −0.35 | |
| | AP5.3 | 11 | 3.40 | 4 | −0.35 | |
| AP5B-A | AP5B.1 | 11 | 6.20 | 9 | −1.21 | Favorable |
| | AP5B.2 | 11 | 4.80 | 2 | −1.21 | |
| AP5B-B | AP5B.3 | 11 | 9.30 | 10 | −0.33 | |
| | AP5B.3 | 11 | 1.70 | 1 | −0.33 | |
| AP5C-A | AP5C.1 | 11 | 10.50 | 11 | −0.23 | |
| | AP5C.1 | 11 | 0.50 | 0 | −0.23 | |
| AP5C-B | AP5C.2 | 11 | 2.40 | 11 | −7.60 | Favorable |
| | AP5C.2 | 11 | 8.60 | 0 | −7.60 | |
| APSC-C | AP5C.3 | 11 | 10.60 | 11 | 0.00 | |
| | AP5C.3 | 11 | 0.40 | 0 | 0.00 | |
| AP5G-A | AP5G.1 | 11 | 2.30 | 1 | −0.55 | |
| | AP5G.1 | 11 | 8.70 | 10 | −0.55 | |
| AP5G-B | AP5G.2 | 11 | 1.30 | 4 | −1.55 | Favorable |
| | AP5G.2 | 11 | 9.70 | 7 | −1.55 | |
| AP5H-A | AP5H.1 | 11 | 6.20 | 8 | −0.66 | |
| | AP5H.1 | 11 | 4.80 | 3 | −0.66 | |
| AP6-A | AP6.2 | 11 | 5.00 | 1 | −1.87 | |
| | AP6.2 | 11 | 6.00 | 10 | −1.87 | Favorable |
| AP7-A | AP7.1 | 11 | 0.50 | 1 | −0.04 | |
| | AP7.1 | 11 | 10.50 | 10 | −0.04 | |
| AP7-B | AP7.2 | 7 | 4.30 | 3 | −0.58 | |
| | AP7.2 | 7 | 2.70 | 4 | −0.58 | |
| AP8B-A | AP8B.1 | 11 | 6.50 | 6 | −0.30 | |
| | AP8B.1 | 11 | 4.50 | 5 | −0.30 | |
| AP8B-B | AP8B.2 | 11 | 9.00 | 10 | −0.44 | |
| | AP8B.2 | 11 | 2.00 | 1 | −0.44 | |
| AP8B-C | AP8B.3 | 11 | 3.60 | 1 | −1.13 | |
| | AP8B.3 | 11 | 7.40 | 10 | −1.13 | Favorable |
| AP8F-A | AP8F.1 | 11 | 5.40 | 2 | −1.47 | |
| | AP8F.1 | 11 | 5.60 | 9 | −1.47 | Favorable |
| AP8H-A | AP8H.1 | 11 | 4.60 | 0 | −2.61 | |
| | AP8H.1 | 11 | 6.40 | 11 | −2.61 | Favorable |

EXAMPLE 2

Use of Genetic Markers to Select Superior Plants

Once markers for QTL's affecting agronomic performance have been identified, the plant breeder will manipulate QTL's the same way he would manipulate qualitatively inherited traits. Applications include:

1) selection of parents that will produce superior transgressive segregants;
2) selection of superior lines from crosses that are segregating at QTL loci;
3) selection of parents that will produce superior hybrids;
4) purification of heterogeneous lines to fix favorable alleles; and
5) selection for and maintenance of desirable heterogeneity.

Examples of each follow:

Selection of Parents to Produce Superior Transgressive Segregants

The goal of plant breeding in general is to produce progeny that exceed their parents in terms of performance for one or more traits. Such progeny are called transgressive segregants. In order to observe transgressive segregation, parents that complement one another in terms of favorable alleles at various loci must be selected. Only then, can crossing and recombination result in progeny that contain more favorable alleles than either parent. For traits such as yield, however, it has been almost impossible to know a priori which parents contain which yield genes. Applicants have now found markers that identify such genes and have provided a basis for selection of parents that contain a different complement of such genes. For example, when examining the marker genotypes of Williams 82 and Essex (Table 6), it becomes apparent that these two lines differ in genotype at 8 out of 17 loci that affect agronomic performance (Table 8). One may, therefore, cross Williams 82 and Essex and will select inbred progeny that contain the favorable allele at all 8 loci. The favorable alleles will contribute to agronomic performance in some additive and/or epistatic fashion, and it will be likely that such progeny will be agronomically superior to either parent.

Selection of Superior Lines From Segregating Populations

Just as markers can be used to select complementary parents that will be used in crosses, the same markers can be used to screen segregating progeny from such crosses. For example, in the Williams 82×Essex cross, progeny lines at various stages of inbreeding will be screened for the favorable allele at all 8 important loci that are segregating. The breeder will select progeny that contain as many of the favorable alleles as possible. The best possible transgressive segregant or "ideal segregant" will be the one that contains the favorable allele at all loci that are segregating (Table 8).

TABLE 8

FAVORABLE ALLELE DISTRIBUTION AND IDEAL SEGREGANT IN WILLIAMS 82 X ESSEX CROSS

| LOCUS | FAVOR-ABLE ALLELE | LOG PROB | WM82 | ES-SEX | IDEAL SEGREGANT |
|---|---|---|---|---|---|
| | | | allele freq w/in line | | |
| 1522-A | 1522.2 | −4.76 | 0 | 1 | 1 |
| 1202-A | 1202.2 | −3.25 | 0 | 1 | 1 |
| 1596-A | 1596.0 | −2.70 | 0 | 1 | 1 |
| AP5G-B | AP5G.2 | −2.09 | 1 | 0 | 1 |
| 1203-A | 1203.0 | −1.91 | 0 | 1 | 1 |
| AP8F-A | AP8F.1NOT | −1.33 | 1 | 0 | 1 |
| 1587-A | 1587.0 | −1.21 | 1 | 0 | 1 |
| AP5B-A | AP5B.1 | −1.12 | 1 | 0 | 1 |
| TOTAL # FAVOR-ABLE ALLELES | | | 4 | 4 | 8 |

By knowing how many important loci are segregating in a particular cross, the breeder will also predict how many progeny lines must be tested to insure that transgressive segregants are found. For example, if progeny from the cross Williams 82×Essex are segregating at 8 important loci, only 1 out of 256 recombinant inbreds (inbred to homozygosity) will contain the favorable allele at all 8 loci. The breeder may also choose to relax his selection intensity. For example, he will select all recombinant inbred lines that contain any combination of 7 or more favorable alleles. By knowing the number of loci involved, the breeder will use standard statistical principles to determine the most efficient method to sample segregants from a given cross.

Selection of Superior Hybrids

In addition to selection of parents that will produce superior recombinant inbreds, complementation at QTL's affecting yield can also be used to predict superior hybrid performance. If one assume that yield genes are generally dominant and/or epistatic in nature, crosses that complement at QTL loci (such as Williams 82×Essex) will also produce good hybrids. Although hybrid seed production is not yet economical for soybeans, Applicants' methods will be used to predict hybrid performance if commercial soybean hybrids become reality. Applicants' methods will also be used to predict hybrid performance within other crop species such as corn, wheat, rice, cotton, vegetable crops, and any species for which hybrid technology is commercially feasible.

Purification of Heterogeneous Lines to Fix Favorable Alleles

According to Table 6, A3307, A3966, A4271, and A5474 are heterogeneous for alleles at at least one important locus. For example, A3307 is segregating at both the 1202-A locus and the 1203-A locus. Presumably this was due to the fact that A3307 was derived from a plant that was not completely inbred and heterozygous at several loci. By bulking up the progeny of a heterozygous plant the resulting population will be a mixture of homozygous plants that segregate at those loci. Unless selection is imposed, the line will remain heterogeneous. Markers for such heterogeneity will permit the breeder to purify such lines and select for the favorable allele at segregating loci. For example, the breeder will select within A3307 for the favorable allele at both the 1202-A and 1203-B locus. Purification of A3307 to enrich favorable alleles will improve the agronomic performance of A3307.

Selection for and Maintenance of Heterogeneity

There will be cases in which heterogeneity is desirable. This will be true if certain loci show allele by environment interactions. For example, in the case of a locus "A" where allele "A1" is necessary for maximum yield in one type of environment and allele "A2" is necessary for maximum yield in another type of environment. In such cases, a population that is heterogeneous for these alleles will be "genetically buffered" and show greater yield stability over both types of environments. Applicants' methods will allow the breeder to select for and maintain such heterogeneity.

In order to identify allele by environment interactions, one will 1) define two (or more) types of environments, 2) classify each elite line into a discrete group based on which environment it performs best in, and 3) determine which alleles are more or less prevalent in one group of lines than another. Alleles occuring more frequently in one group than another will be those that are favored by the environment used to classify that group.

To confirm whether intra-line heterogeneity at a specific locus will be beneficial for agronomic performance, one will 1) identify lines that are heterogeneous for the locus in question 2) develop sub-populations of the line that are homogeneous for one or the other allele based on selection with Applicants' markers, 3) field test the original heterogeneous line along with each of derived homogeneous lines over a number of defined environments, and 4) determine whether the heterogeneous line will perform (yield) better than either homogeneous line when averaged over all test environments.

EXAMPLE 3

Demonstrating Utility of Informative Probes (A3127 Case)

In Example 1, the cross Williams 82×Essex was shown to be polymorphic at 8 agronomically important loci (Table 8). Based on the ancestral/elite survey, we have also determined which allele at each of the important loci was favorable (Table 8). Williams 82 has the desirable allele at 4 out of the 8 relevant loci and Essex has the desirable allele at the other 4 loci. Crossing these two parents provides the opportunity to produce progeny that contain 5, 6, 7, or all 8 of the favorable alleles and are agronomically superior to either parent. Using Applicants' method to select among segregants from the Williams 82×Essex cross, one would simply select for segregants that have as many of the favorable alleles as possible.

One could presumably test the effectiveness of Applicants' method by crossing Williams 82 with Essex, and measuring the correlation between yield and number of desirable alleles among random inbred progeny lines from the cross. However, as discussed in the Background of the Invention section, obtaining a reliable measure of the yield potential of each segregant would require highly replicated field testing. Alternatively, Applicants can examine the genotype of known transgressive segregants that have been identified previously through exhaustive yield testing. One such transgressive segregant is the variety A3127.

A3127 represents a landmark in the history of soybean breeding. It was recognized as not only a transgressive yield segregant from the cross Williams×Essex but as the standard of the industry in the early 1980's in terms of yield regardless of pedigree. Since Williams 82 is a near isogenic line of Williams (Williams 82=Williams[7]×Kingwa=99% identical to Williams), results of the Williams×Essex cross should be directly relevant to the Williams 82×Essex cross. One would, therefore, expect A3127 (a proven transgressive yield segregant) to contain more favorable alleles for yield than either Williams 82 or Essex.

Table 9 shows the actual genotype of A3127 compared to Williams 82, Essex, and the ideal transgressive segregant. A3127, with 7 out of 8 possible favorable alleles, exceeds both Williams 82 and Essex in terms of the number of favorable alleles. The probability of A3127 having 7 out of 8 possible favorable alleles due to random chance alone is only 1 in 32. It is, therefore, clear that the correlation between agronomic performance of A3127 and its genotype regarding Applicants' favorable alleles is not random. This is direct evidence that Applicants' favorable alleles are truly associated with superior agronomic performance. Although A3127 was selected through exhaustive yield testing, such a line could have been selected in the laboratory using Applicants' methods. In fact, the existing data suggest that an even better segregant than A3127 could have been selected from the Williams×Essex cross if Applicants' method was used. Such a segregant would have all 8 favorable alleles such as the "ideal segregant" proposed in Table 9.

TABLE 9

| | TRANSGRESSIVE SEGREGATION IN A3127 | | | | | |
|---|---|---|---|---|---|---|
| LOCUS | FAVORABLE ALLELE | LOG PROB | WM82 | ESSEX | IDEAL SEGREGANT | A3127 |
| | | | allele freq w/in line | | | |
| 1522-A | 1522.2 | −4.76 | 0 | 1 | 1 | 1 |
| 1202-A | 1202.2 | −3.25 | 0 | 1 | 1 | 1 |
| 1596-A | 1596.0 | −2.70 | 0 | 1 | 1 | 1 |
| AP5G-B | AP5G.2 | −2.09 | 1 | 0 | 1 | 0 |
| 1203-A | 1203.0 | −1.91 | 0 | 1 | 1 | 1 |
| AP8F-A | AP8F.1NOT | −1.33 | 1 | 0 | 1 | 1 |
| 1587-A | 1587.0 | −1.21 | 1 | 0 | 1 | 1 |
| AP5B-A | AP5B.1 | −1.12 | 1 | 0 | 1 | 1 |
| TOTAL # FAVORABLE ALLELES | | | 4 | 4 | 8 | 7 |

EXAMPLE 4

Demonstrating Utility of Informative Probes (A3966 Case)

Like A3127, A3966 is also a transgressive yield segregant from the cross Williams×Essex. A3966 was selected independently of A3127 but was subjected to the same rigorous yield testing before it was identified as superior to its parents. One would expect A3966 to contain more of Applicants' favorable alleles than Williams 82 or Essex.

A3966 had 6.5 (segregating for allele 1203.0) out of 8 possible favorable alleles (Table 10). This exceeds both Williams 82 and Essex in terms of the number of favorable alleles. As with the case of A3127, the genotype of A3966 is also direct evidence of the applicability of Applicants' methods. Although A3966 was selected through exhaustive yield testing, such a line could have been selected in the laboratory using Applicants' methods. In fact, Applicants' data suggest that an even better segregant than A3966 could have been selected from the Williams×Essex cross if Applicants' methods had been used. Such a segregant would have all 8 favorable alleles such as the "ideal segregant" proposed in Table 10.

Another conclusion that can be drawn is that A3127 and A3966, although derived from the same cross, are different at three important yield loci (1522-A, AP5G-B, and 1203-A—see Table 10). Although one might assume that little genetic variation exists between these two lines, Applicants' markers can be used to track the remaining variation that is important. One could obtain a segregant from the A3127×A3966 cross that exceeds either parent in terms of the numbers of favorable yield genes (Table 10). With the available markers, one could select the "ideal segregant" more frequently from the A3127×A3966 cross than the Williams×Essex cross since more of the favorable alleles would already be fixed in the former cross. Instead of 8 loci segregating, only 3 loci would be segregating at most. This would increase the frequency of the "ideal segregant" among inbred progeny from 1 in 256 to 1 in 8.

TABLE 10

TRANSGRESSIVE SEGREGATION IN A3966

| LOCUS | FAVORABLE ALLELE | LOG PROB | WM82 | ESSEX | IDEAL SEGREGANT | A3127 | A3966 |
|---|---|---|---|---|---|---|---|
| | | | \multicolumn{5}{c}{allele freq w/in line} | | | | |
| 1522-A | 1522.2 | −4.76 | 0 | 1 | 1 | 1 | 0 |
| 1202-A | 1202.2 | −3.25 | 0 | 1 | 1 | 1 | 1 |
| 1596-A | 1596.0 | −2.70 | 0 | 1 | 1 | 1 | 1 |
| AP5G-B | AP5G.2 | −2.09 | 1 | 0 | 1 | 0 | 1 |
| 1203-A | 1203.0 | −1.91 | 0 | 1 | 1 | 1 | .5 |
| AP8F-A | AP8F.1NOT | −1.33 | 1 | 0 | 1 | 1 | 1 |
| 1587-A | 1587.0 | −1.21 | 1 | 0 | 1 | 1 | 1 |
| AP5B-A | AP5B.1 | −1.12 | 1 | 0 | 1 | 1 | 1 |
| | TOTAL # FAVORABLE ALLELES | | 4 | 4 | 8 | 7 | 6.5 |

---

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:
        TCCTAGCCAA ( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TCTCGATGCA ( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTGATGCTAC ( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CTCTTGCTAC ( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CTCATGCATC ( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CACATGCTTC ( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCAAGTAGCT ( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

CTGATACGGA ( 2 ) INFORMATION FOR SEQ ID NO:9:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TCGTCACTGA ( 2 ) INFORMATION FOR SEQ ID NO:10:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

TGGTCTCTGA ( 2 ) INFORMATION FOR SEQ ID NO:11:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

CTGAAGTAC

What is claimed is:
1. A method for identifying alleles associated with agronomic fitness of soybean comprising:
   a) selecting a sample of current-day elite lines of soybean to form an elite population;
   b) selecting the predominant and earliest known ancestral lines of said elite lines by considering the pedigrees of said elite lines;
   c) conducting a genetic marker survey to determine the genotype of said elite lines and said ancestral lines;
   d) using the pedigrees of said elite lines and genotypes of said ancestral lines to calculate the probability of each elite line inheriting each allele from said ancestral lines;
   e) calculating the expected allele frequency of each allele within said elite population by averaging the probabilities calculated in step d) for each elite line;
   f) calculating the observed allele frequency within said elite population;
   g) comparing said observed allele frequency with said expected allele frequency for each said allele in said elite population to identify alleles at each locus that have been inherited more frequently than expected; and
   h) producing soybean plants with superior agronomic fitness;
such that said soybean plants with superior agronomic fitness can be efficiently identified with said genetic markers that are diagnostic of said alleles that have been inherited more frequently than expected.

2. A method of claim 1, wherein in step c) the genetic marker is selected from the group consisting of 1202, 1443, 1522, 1525, 1596, 1203, 1329, 1529, 1593, 1587, AP5C, AP5G, AP8H, AP6, AP8F, AP4C, and AP5B is used to conduct said genetic marker survey.

3. A method for breeding agronomically superior soybean plants, comprising:
   a) identifying the genotype of a number of soybean lines by conducting a genetic marker survey using a genetic marker selected from the group consisting of 1202, 1443, 1522, 1525, 1596, 1203, 1329, 1529, 1593, 1587, AP5C, AP5G, AP8H, AP6, AP8F, AP4C, and AP5B; and
   b) selecting parent soybean lines identified in step a) that, when crossed, produce an ideal segregant containing more favorable alleles than either parent.

4. A method of claim 1 wherein step g) is performed using a chi-squared test for the statistical significance of the deviation of observed allele frequency from expected allele frequency.

5. A method of claim 1 wherein step g) is performed by computing the distribution of possible allele counts by the generalized binomial distribution, and using said binomial distribution to compute a cumulative probability that provides a statistical measure of the significance of the deviation of observed allele frequency from expected allele frequency.

* * * * *